United States Patent
Gibbs et al.

(10) Patent No.: US 7,291,711 B2
(45) Date of Patent: Nov. 6, 2007

(54) FLUORESCENT PROTEINS FROM AQUATIC SPECIES

(75) Inventors: Patrick D. L. Gibbs, Miami, FL (US); Robert W. Carter, Miami, FL (US); Michael C. Schmale, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 11/021,014

(22) Filed: Dec. 23, 2004

(65) Prior Publication Data

US 2005/0100954 A1    May 12, 2005

Related U.S. Application Data

(62) Division of application No. 10/314,936, filed on Dec. 9, 2002.

(51) Int. Cl.
C07K 1/00 (2006.01)
(52) U.S. Cl. .................. 530/350; 435/69.1; 435/6; 435/252; 435/320; 530/300; 530/350; 536/23.1
(58) Field of Classification Search ............... 435/69.1, 435/7.1; 424/192.1; 530/350, 300; 514/2, 514/12
See application file for complete search history.

(56) References Cited

U.S. PATENT DOCUMENTS

| | | | |
|---|---|---|---|
| 4,968,613 A | 11/1990 | Masuda | |
| 5,096,825 A | 3/1992 | Barr | |
| 5,182,202 A | 1/1993 | Kajiyama | |
| 5,219,737 A | 6/1993 | Kajiyama | |
| 5,229,285 A | 7/1993 | Kajiyama | |
| 5,283,179 A | 2/1994 | Wood | |
| 5,292,658 A | 3/1994 | Cormier | |
| 5,330,906 A | 7/1994 | Kajiyama | |
| 5,352,598 A | 10/1994 | Kajiyama | |
| 5,418,155 A | 5/1995 | Cormier | |
| 5,583,024 A | 12/1996 | McElroy | |
| 5,604,123 A | 2/1997 | Kazami | |
| 5,641,641 A | 6/1997 | Wood | |
| 5,650,289 A | 7/1997 | Wood | |
| 5,670,356 A | 9/1997 | Sherf et al. | |
| 5,674,713 A | 10/1997 | McElroy | |
| 5,700,673 A | 12/1997 | McElroy | |
| 5,744,320 A | 4/1998 | Sherf | |
| 5,786,464 A | 7/1998 | Seed | |
| 5,795,737 A | 8/1998 | Seed et al. | |
| 5,874,304 A | 2/1999 | Zolotukhin et al. | |
| 5,952,547 A | 9/1999 | Cornelissen et al. | |
| 5,968,750 A | 10/1999 | Zolotukhin | |
| 5,976,796 A | 11/1999 | Szalay | |
| 6,020,192 A | 2/2000 | Muzyczka | |
| 6,074,859 A | 6/2000 | Hirokawa | |
| 6,169,232 B1 | 1/2001 | Hey et al. | |
| 6,342,379 B1 | 1/2002 | Tsien et al. | 435/173.4 |
| 6,414,119 B1 | 7/2002 | Fisher | 530/350 |
| 6,689,391 B2 | 2/2004 | Goswami et al. | 424/559 |
| 6,723,537 B2 | 4/2004 | Peelle | 435/69.1 |
| 6,900,304 B2 | 5/2005 | Tsien et al. | |
| 2002/0064842 A1 | 5/2002 | Sorge et al. | 435/183 |
| 2002/0107362 A1 | 8/2002 | Thastrup et al. | 530/350 |
| 2003/0106078 A1 | 6/2003 | Falkowski et al. | 800/8 |
| 2003/0157643 A1* | 8/2003 | Almond et al. | 435/69.1 |
| 2005/0032085 A1 | 2/2005 | Labas et al. | |

FOREIGN PATENT DOCUMENTS

| | | |
|---|---|---|
| WO | 95/25798 | 9/1995 |
| WO | 96/22376 | 7/1996 |
| WO | 97/26366 | 7/1997 |
| WO | WO 97/28261 | 8/1997 |
| WO | 97/47358 | 12/1997 |
| WO | 99/14336 | 3/1999 |
| WO | WO 00/34526 | 6/2000 |
| WO | WO 01/27150 A2 | 4/2001 |
| WO | WO 01/62919 A1 | 8/2001 |
| WO | WO 02/16944 A2 | 2/2002 |
| WO | WO 02/094992 A2 | 11/2002 |
| WO | WO 03/042401 A2 | 5/2003 |
| WO | WO 03/042401 A3 | 5/2003 |

OTHER PUBLICATIONS

Fradkov et al., FEBS Letters, vol. 479, pp. 127-130, 2000.*
Seffernick et al., J. Bacteriology, vol. 183, pp. 2405-2410, 2001.*
Wells, Biochemistry, vol. 29, pp. 8509-8517, 1990.*
GenBank Accession No. AF401282. (Aug. 2001).
Pan W. et al "Vaccine Candidate MSP-I from Plasmodium Falciparum: a Redesigned 4917 bp Polynucleotide Enables Synthesis and Isolation of Full-Length Protein from *Escherichia coli* and Mammalian Cells," Nuc. Acids Res., vol. 27, No. 4, 1094-1103 (1999).
Andrews, "Hierarchy of polyadenylation site usage by bovine papillomavirus in transformed mouse cells," J. Virology, (1993) p. 7705-7710, 67(12).
Benzakour, "Evaluation of the use of the luciferase-reporter-gene system for gene-regulation studies . . . " Charter Molecular Genetics Lab (1995), p. 385-387.

(Continued)

*Primary Examiner*—Hope Robinson
(74) *Attorney, Agent, or Firm*—Whyte Hirschboeck Dudek S.C.

(57) ABSTRACT

Provided are four new fluorescent proteins. The proteins were derived from two wild-type fluorescent proteins: a red fluorescent protein (RFP) that was isolated from *Actinodiscus* or *Discosoma* sp. 1 and a green fluorescent protein (GFP) isolated from *Montastraea cavernosa*. Two mutant forms were generated from each wild-type protein. Each of the mutated forms has a higher fluorescence intensity than the respective wild-type form. The mutant forms of the fluorescent proteins allow for more sensitive detection of the fluorescence emitted by the proteins. Additionally, one of the mutant proteins is more resistant to photobleaching than its wild-type protein. The invention also encompasses isolated nucleic acids encoding the mutant forms of the wild-type RFP and GFP.

8 Claims, 12 Drawing Sheets

OTHER PUBLICATIONS

Cameron, "Recent advances in transgenic technology," Molecular Biotechnology (1997, p. 253-265, v. 7.

Chen, "Gene transfer and expression in oligodendrocytes under the control of myelin basic protein transcriptional control region . . . " Gene Therapy (1998), p. 50-58, v. 5.

Coker, "8-Br-cAMP inhibits the transient expression of firefly luciferase," FEBS Letters (1989), p. 183-84, v. 249(2).

Faisst, "Compilation of vertebrate-encoded transcription factors," Nucleic Acids Research (1992), p. 3-26, v. 20(1).

GENBANK AY037770, Montastraea cavernosa green fluorescent protein mRNA (2001).

GENBANK AY056460, *Montastraea cavernosa* cyan fluorescent protein mRNA (2001).

Glass, "Gene functions: *E. coli* and its heritable elements," RNA and Protein Productions (1982), p. 95, U. California Press.

Gruber, "Design strategy for synthetic luciferase reporter genes," 11th Symposium on Bioluminescence & Chemiluminescence (2000), abstract.

Henning, "Humanizing the yeast telomerase template," Proc. Natl. Acad. Science (1998), p. 5667-5671, v. 95, USA.

Hsieh, "Nucleotide sequence, transcriptional analysis, and glucose regulation of the phenoxazinone synthase gene (phsA) . . . ," J. Bacteriology (1995), p. 5740-5747, 177(2).

Jensen, "The sequence of spacers between the consensus sequences modulates the strength of prokaryotic promoters," Applied. and Environmental. Microbiology (1998), p. 82-87, 64(1).

Kappel, "Regulating gene expression in transgenic animals," Current Opinions in Biotechnology (1992), p. 548-553, v. 3.

Kimura, "Detailed analysis of the mouse H-2Kb promoter: enhancer-like sequences and their role in the regulation of class I gene expression," Cell (1986), p. 261-272, v. 44.

Kozak, "An analysis of 5'-noncoding sequences from 699 vertebrate messenger RNAs," Nucleic Acids Research (1987), p. 8125-8132, 15(20).

Labas, "Diversity and evolution of the green fluorescent protein family," PNAS (2002), p. 4256-4261, 99(7).

Liu, "Improved assay sensitivity of an engineered secreted Renilla luciferase," Gene (1999), p. 153-159, v. 237.

Lodish, "Spliceosomes, assembled from snRNPs and a Pre-mRNA, carry out splicing," Molecular Cell Biology (2000) p. 416-418.

Mount, "Genomic sequence, splicing, and gene annotation," Am. J. Human Genetics (2000), p. 788-792, v. 67.

Mullins, John J., "Transgenesis in nonmurine species," Hypertension (1993), p. 630-633, 22(4).

Mullins, Linda, "Molecular medicine in genetically engineered animals," J. Clin. Invest. (1996) p. 1157-1560, 97(7).

Murray, "Codon usage in plant genes," Nucleic Acids Research (1988) p. 477-498, 17(2).

Peers, "Regulatory elements controlling pituitary-specific expression of the human prolactin gene," Molecular and Cellular Biology (1990) p. 4690-4700, v. 10.

Quandt, "Matlnd and Malnspector: new fast and versatile tools for detection of consensus matches in nucleotide sequence data," Nucleic Acids Research (1995) p. 4878-4884, 23(23).

Ringquist, "Translation initiation in *Escherichia coli*: sequences within the ribosome-binding site," Molecular Microbiology (1992) p. 1219-1229, 6(9).

Sala-Newby, "Engineering firefly luciferase as an indicator of cyclic AMP-dependent protein kinase in living cells," FEBS Letters (1992), p. 241-244, 307(2).

Schatt, "A single DNA-binding transcription factor is sufficient for activation from a distant enhancer and/or from a promoter position," The EMBO J. (1990) p. 481-487, 9(2).

Seffernick, "Melamine deaminase and atrazine chlorohydrolase: 98 percent identical but functionally different," J. of Bacteriology (2001) p. 2404-2410, 183(8).

Sharp, "Codon usage patterns in *Escherichia coli, Bacillus subtilis, . . . *", Nucleic Acids Research (1988) p. 8207-8211, 16(17).

Sharp, "The codon adaptation index-a measure of directional synonymous codon usage bias . . . ", Nucleic Acids Research (1987) p. 1281-1294, 15(3).

Sherf, "Firefly luciferase engineered for improved genetic reporting," PNotes Magazine (1994), p. 14(8 pages), No. 49, Promega Corporation, Madison, Wisconsin.

Tabaska, "Detection of polyadenylation signals in human DNA sequences," Gene (1999) p. 77-86, 231.

Viviani, "Bioluminescence color determinants of Phrixothrix railroad-worm luciferases: . . . ," Photochemistry and Photobiology (2000) p. 267-271, 72(2).

Wada, "Codon usage tabulated from the GenBank genetic sequence data," Nucleic Acids Research Supplement (1990) p. 2367-2411, v. 18.

Wells, "Additivity of mutational effects in proteins," Biochemistry (1990) p. 8511-8517, 29(37).

Wigley, "Site-specific transgene insertion: an approach," Reprod. Fertil. Dev. (1994) p. 585-588, 6(5).

Yang, "Human dihydrofolate reductase gene organization," J. Molecular Biology (1984) p. 169-187, v. 176.

Dorsky, Richard I. et al., "A transgenic Lefl/beta-catenin-dependent reporter is expressed in spatially restricted domains throughout zebrafish development," Developmental Biology, 2002, pp. 229-237, vol. 241.

Liu et al., *Is Green Fluorescent Protein Toxic to the Living Cells?*, May 1999, Biochemical and Biophysical Research Communications 260, pp. 712-717.

Chalfie et al., *Green Fluorescent Protein as a Marker for Gene Expression*, Feb. 1994, SCIENCE, vol. 263, pp. 802-805.

Fautin et al., *Two New Species of Deep-Water Corallimorpharia (Cnidaria:Anthozoa) from the Northeast Pacific, Corallimorphus denhartogi and C.pilatus*, Apr. 2002, Pacific Science, vol. 56, No. 2:113-124, pp. 113-124.

Yang et al., *The Molecular Structure of Green Fluorescent Protein*, Oct. 1996, Nature Biotechnology, vol. 14, pp. 1246-1251.

Yokoe et al., *Spatial Dynamics of GEP-tagged Proteins Investigated by Local Fluorescence Enhancement*, Oct. 1996, Nature Biotechnology, vol. 14, pp. 1252-1256.

Ormo et al. *Crystal Structure of the Aequorea Victoria Green Fluorescent Protein*, Sep. 1996, SCIENCE, vol. 273, pp. 1392-1395.

Miyawaki, *Green Fluorescent Protein-like Proteins in Reef Anthozoa Animals*, 2002, Cell Structure and Function 27, pp. 343-347.

Gibbs et al., *GFP as a Genetic Marker Scorable Throughout the Life Cycle of Transgenic Zebra Fish*, Mar./Apr. 200, Marine Biotechnology, vol. 2, No. 2, pp. 126.

Wiehler et al., *Mutants of Discosoma Red Fluorescent Protein with a GFP-like Chromophore*, FEBS Letters 487 (2001), pp. 384-389.

Fradkov et al., *Novel Fluorescent Protein from Discosomoa Coral and its Mutants Possess a Unique Far-Red Fluorescence*, FEBS Letters 479 (2000), pp. 127-130.

Matz et al., *Fluorescent Proteins from Nonbioluminescent Anthozoa Species*, Nature Biotechnology, vol. 17, Oct. 1999, pp. 969-973.

Clontech, *Living Colors Red Fluorescent Protein*, CLONTECHniques, Oct. 1999, pp. 1-5.

Prasher et al., *Primary Structure of the Aequorea victoria Green-Fluorescent Protein*, 1992, GENE, pp. 229-233.

Dove et al., *Major Colour Patterns of Reef-building Corals are Due to a Family of GFP-like Proteins*, 2001, Coral Reefs, pp. 197-204.

\* cited by examiner

FIG. 1A

```
                                                                          Section 1
              (1) 1         10        20        30        40        52
      RedI   (1) ATGAGTTGTTCCAAGAATGTTATCAAGGAGTTCATGAGGTTTAAGGTTCGTA
      RedII  (1) ATGAGTTGTTCCAAGAATGTTATCAAGGAGTTCATGAGGTTTAAGGTTCGTA
  Consensus  (1) ATGAGTTGTTCCAAGAATGTTATCAAGGAGTTCATGAGGTTTAAGGTTCGTA
                                                                          Section 2
             (53) 53        60        70        80        90       104
      RedI  (53) TGGAAGGAACGGTCAATGGGCACGAGTTTGAAATAGAAGGCGAAGGAGAAGG
      RedII (53) TGGAAGGAACGGTCAATGGGCACGAGTTTGAAATAGAAGGCGAAGGAGAAGG
  Consensus (53) TGGAAGGAACGGTCAATGGGCACGAGTTTGAAATAGAAGGCGAAGGAGAAGG
                                                                          Section 3
            (105) 105   110       120       130       140       156
      RedI (105) GAGGCCATACGAAGGCCACAATACCGTAAAGCTTAAGGTAACCAAGGGGGA
      RedII(105) GAGGCCATACGAAGGCCACAATACCGTAAAGCTTAAGGTAACCAAGGGGGA
  Consensus(105) GAGGCCATACGAAGGCCACAATACCGTAAAGCTTAAGGTAACCAAGGGGGA
                                                                          Section 4
            (157) 157       170       180       190       208
      RedI (157) CCTTTGCCATTTGCTTGGGATATTTTGTCACCACAATTTCAGTATGGAAGCA
      RedII(157) CCTTTGCCATTTGCTTGGGATATTTTGTCACCACAATTTCAGTATGGAAGCA
  Consensus(157) CCTTTGCCATTTGCTTGGGATATTTTGTCACCACAATTTCAGTATGGAAGCA
                                                                          Section 5
            (209) 209       220       230       240       250       260
      RedI (209) AGGTATATGTCAAGCATCCTGCCGACATACCAGACTATAAAAAGCTGTCATT
      RedII(209) AGGTATATGTCAAGCATCCTGCCGACATACCAGACTATAAAAAGCTGTCATT
  Consensus(209) AGGTATATGTCAAGCATCCTGCCGACATACCAGACTATAAAAAGCTGTCATT
                                                                          Section 6
            (261) 261       270       280       290       300       312
      RedI (261) TCCTGAAGGATTTAAATGGGAAAGGGTCATGAACTTTGAAGACGGTGGCGTC
      RedII(261) TCCTGAAGGATTTAAATGGGAAAGGGTCATGAACTTTGAAGACGGTGGCGTC
  Consensus(261) TCCTGAAGGATTTAAATGGGAAAGGGTCATGAACTTTGAAGACGGTGGCGTC
                                                                          Section 7
            (313) 313       320       330       340       350       364
      RedI (313) GTTACTGTAACCCAGGATTCCAGTTTGCAGGATGGCTGTTTCATCTACAAGG
      RedII(313) GTTACTGTAACCCAGGATTCCAGTTTGCAGGATGGCTGTTTCATCTACAAGG
  Consensus(313) GTTACTGTAACCCAGGATTCCAGTTTGCAGGATGGCTGTTTCATCTACAAGG
                                                                          Section 8
            (365) 365       370       380       390       400       416
      RedI (365) TCAAGTTCATTGGCGTGAACTTTCCTTCTGATGGACCTGTTATGCAAAAGAA
      RedII(365) TCAAGTTCATTGGCGTGAACTTTCCTTCTGATGGACCTGTTATGCAAAAGAA
  Consensus(365) TCAAGTTCATTGGCGTGAACTTTCCTTCTGATGGACCTGTTATGCAAAAGAA
```

FIG. 1B

```
                                                                               Section 9
            (417) 417           430         440          450             468
       RedI (417) GACAATGGGCTGGGAAGCCAGCACTGAGCGTTTGTATCCTCGTGATGGCGTG
      RedII (417) GACAATGGGCTGGGAAGCCAGCACTGAGCGTTTGTATCCTCGTGATGGCGTG
  Consensus (417) GACAATGGGCTGGGAAGCCAGCACTGAGCGTTTGTATCCTCGTGATGGCGTG
                                                                              Section 10
            (469) 469           480         490          500         510      520
       RedI (469) TTGAAAGGAGAGATTCATAAGGCTCTGAAGTTGAAAGACGGTGGTCATTACC
      RedII (469) TTGAAAGGAGAGATTCATAAGGCTCTGAAGTTGAAAGACGGTGGTCATTACC
  Consensus (469) TTGAAAGGAGAGATTCATAAGGCTCTGAAGTTGAAAGACGGTGGTCATTACC
                                                                              Section 11
            (521) 521          530         540         550          560       572
       RedI (521) TAGTTGAATTCAAAACTATTTACATGGCAAAGAAGCCTGTGCAGCTACCAGG
      RedII (521) TAGTTGAATTCAAAACTATTTACATGGCAAAGAAGCCTGTGCAGCTACCAGG
  Consensus (521) TAGTTGAATTCAAAACTATTTACATGGCAAAGAAGCCTGTGCAGCTACCAGG
                                                                              Section 12
            (573) 573       580        590         600          610           624
       RedI (573) GTACTACTATGTTGACTCCAAACTGGATATAACAAGCCACAACAAAGACTAT
      RedII (573) GTACTACTATGTTGACTCCAAACTGGATATAACAAGCCACAACAAAGACTAT
  Consensus (573) GTACTACTATGTTGACTCCAAACTGGATATAACAAGCCACAACAAAGACTAT
                                                                              Section 13
            (625) 625      630          640            650         660        676
       RedI (625) ACAATCGTTGAGCAGTATGAAAGAACCGAGGGACGCCACCATCTGTTCCTTA
      RedII (625) ACAATCGTTGAGCAGTATGAAAGAACCGAGGGACGCCACCATCTGTTCCTTA
  Consensus (625) ACAATCGTTGAGCAGTATGAAAGAACCGAGGGACGCCACCATCTGTTCCTTA
                                                                              Section 14
            (677) 677           690          700         711
       RedI (677) AGGCTGAACTTGGCTCAGACGTGGGTGAGCGGTAA
      RedII (677) AGGCTGAACTTGGCTCAAACGTGGGTGAGCGGTAA
  Consensus (677) AGGCTGAACTTGGCTCA ACGTGGGTGAGCGGTAA
```

FIG. 2

```
                                                                              Section 1
            (1) 1         10         20         30         40        52
   RedIaa   (1) MSCSKNVIKEFMRFKVRMEGTVNGHEFEIEGEGEGRPYEGHNTVKLKVTKGG
   RedIIaa  (1) MSCSKNVIKEFMRFKVRMEGTVNGHEFEIEGEGEGRPYEGHNTVKLKVTKGG
   Consensus (1) MSCSKNVIKEFMRFKVRMEGTVNGHEFEIEGEGEGRPYEGHNTVKLKVTKGG
                                                                              Section 2
           (53) 53        60         70         80         90       104
   RedIaa  (53) PLPFAWDILSPQFQYGSKVYVKHPADIPDYKKLSFPEGFKWERVMNFEDGGV
   RedIIaa (53) PLPFAWDILSPQFQYGSKVYVKHPADIPDYKKLSFPEGFKWERVMNFEDGGV
   Consensus (53) PLPFAWDILSPQFQYGSKVYVKHPADIPDYKKLSFPEGFKWERVMNFEDGGV
                                                                              Section 3
           (105) 105      110       120        130        140       156
   RedIaa (105) VTVTQDSSLQDGCFIYKVKFIGVNFPSDGPVMQKKTMGWEASTERLYPRDGV
   RedIIaa (105) VTVTQDSSLQDGCFIYKVKFIGVNFPSDGPVMQKKTMGWEASTERLYPRDGV
   Consensus (105) VTVTQDSSLQDGCFIYKVKFIGVNFPSDGPVMQKKTMGWEASTERLYPRDGV
                                                                              Section 4
           (157) 157       170       180        190                  208
   RedIaa (157) LKGEIHKALKLKDGGHYLVEFKTIYMAKKPVQLPGYYYVDSKLDITSHNKDY
   RedIIaa (157) LKGEIHKALKLKDGGHYLVEFKTIYMAKKPVQLPGYYYVDSKLDITSHNKDY
   Consensus (157) LKGEIHKALKLKDGGHYLVEFKTIYMAKKPVQLPGYYYVDSKLDITSHNKDY
                                                                              Section 5
           (209) 209       220       236
   RedIaa (209) TIVEQYERTEGRHHLFLKAELGSDVGER
   RedIIaa (209) TIVEQYERTEGRHHLFLKAELGSNVGER
   Consensus (209) TIVEQYERTEGRHHLFLKAELGS VGER
```

FIG. 6A

```
                                                                    Section 1
              (1) 1        10         20        30        40       52
    GreenI    (1) ATGAGTGTGATAAAACCAGACATGAAGATCAAGCTGCGTATGGAAGGTGCTG
    GreenII   (1) ATGAGTGTGATAAAACCAGACATGAAGATCAAGCTGCGTATGGAAGGTGCTG
    Consensus (1) ATGAGTGTGATAAAACCAGACATGAAGATCAAGCTGCGTATGGAAGGTGCTG
                                                                    Section 2
             (53) 53        60        70        80        90       104
    GreenI   (53) TAAACGGGCACAAGTTCGTGATTGAAGGAGACGGAAAAGGCAAGCCTTTCGA
    GreenII  (53) TAAACGGGCACAAGTTCGTGATTGAAGGAGACGGAAAAGGCAAGCCTTTCGA
    Consensus(53) TAAACGGGCACAAGTTCGTGATTGAAGGAGACGGAAAAGGCAAGCCTTTCGA
                                                                    Section 3
             (105) 105   110       120       130       140         156
    GreenI   (105) GGGAAAACAGACTATGGACCTTACAGTCATAGAAGGCGCACCTTTGCCTTTC
    GreenII  (105) GGGAAAACAGACTATGGACCTTACAGTCATAGAAGGCGCACCTTTGCCTTTC
    Consensus(105) GGGAAAACAGACTATGGACCTTACAGTCATAGAAGGCGCACCTTTGCCTTTC
                                                                    Section 4
             (157) 157        170       180       190              208
    GreenI   (157) GCTTACGATATCTTGACAACAGTATTCGATTACGGCAACAGGGTATTCGCCA
    GreenII  (157) GCTTACGATATCTTGACAACAGTATTCGATTACGGCAACAGGGTATTCGCCA
    Consensus(157) GCTTACGATATCTTGACAACAGTATTCGATTACGGCAACAGGGTATTCGCCA
                                                                    Section 5
             (209) 209        220       230       240       250    260
    GreenI   (209) AATACCCAAAAGACATACCAGACTATTTCAAGCAGACGTTTCCGGAGGGGTA
    GreenII  (209) AATACCCAAAAGACATACCAGACTATTTCAAGCAGACGTTTCCGGAGGGGTA
    Consensus(209) AATACCCAAAAGACATACCAGACTATTTCAAGCAGACGTTTCCGGAGGGGTA
                                                                    Section 6
             (261) 261       270       280       290       300     312
    GreenI   (261) CTCCTGGGAACGAAGCATGACATACGAAGACCAGGGCATTTGCATCGCCACA
    GreenII  (261) CTCCTGGGAACGAAGCATGACATACGAAGACCAGGGCATTTGCATCGCCACA
    Consensus(261) CTCCTGGGAACGAAGCATGACATACGAAGACCAGGGCATTTGCATCGCCACA
                                                                    Section 7
             (313) 313       320       330       340       350     364
    GreenI   (313) AACGACATAACAATGATGAAAGGCGTCGACGACTGTTTTGTCTATAAAATTC
    GreenII  (313) AACGACATAACAATGATGAAAGGCGTCGACGACTGTTTTGTCTATAAAATTC
    Consensus(313) AACGACATAACAATGATGAAAGGCGTCGACGACTGTTTTGTCTATAAAATTC
                                                                    Section 8
             (365) 365   370       380       390       400         416
    GreenI   (365) GATTTGATGGTGTGAACTTTCCTGCCAATGGTCCAGTTATGCAGAGGAAGAC
    GreenII  (365) GATTTGATGGTGTGAACTTTCCTGCCAATGGTCCAGTTATGCAGAGGAAGAC
    Consensus(365) GATTTGATGGTGTGAACTTTCCTGCCAATGGTCCAGTTATGCAGAGGAAGAC
```

FIG. 6B

```
                                                                            Section 9
         (417) 417          430         440        450              468
   GreenI (417) GCTAAAATGGGAGCCATCCACTGAAAAAATGTATGTGCGTGATGGGGTACTG
  GreenII (417) GCTAAAATGGGAGCCATCCACTGAAAAAATGTATGTGCGTGATGGGGTACTG
Consensus (417) GCTAAAATGGGAGCCATCCACTGAAAAAATGTATGTGCGTGATGGGGTACTG
                                                                            Section 10
         (469) 469         480        490        500       510      520
   GreenI (469) AAGGGTGATGTTAACATGGCTCTGTTGCTTGAAGGAGGTGGCCATTACCGAT
  GreenII (469) AAGGGTGATGTTAACATGGCTCTGTTGCTTGAAGGAGGTGGCCATTACCGAT
Consensus (469) AAGGGTGATGTTAACATGGCTCTGTTGCTTGAAGGAGGTGGCCATTACCGAT
                                                                            Section 11
         (521) 521        530       540        550        560        572
   GreenI (521) GTGACTCCAAAACTACTTACAAAGCTAAGAAGGTTGTCCAGTTGCCAGACTA
  GreenII (521) GTGACTTCAAAACTACTTACAAAGCTAAGAAGGTTGTCCAGTTGCCAGACTA
Consensus (521) GTGACT CAAAACTACTTACAAAGCTAAGAAGGTTGTCCAGTTGCCAGACTA
                                                                            Section 12
         (573) 573      580         590        600       610         624
   GreenI (573) TCATTTTGTTGACCATCGCATTGAGATTGTGAGCCACGACAAAGATTACAAC
  GreenII (573) TCATTTTGTTGACCATCGCATTGAGATTGTGAGCCACGACAAAGATTACAAC
Consensus (573) TCATTTTGTTGACCATCGCATTGAGATTGTGAGCCACGACAAAGATTACAAC
                                                                            Section 13
         (625) 625     630         640        650         660         676
   GreenI (625) AAGGTTAAGCTGTATGAGCATGCCGAAGCTCATTCTGGGCTGCCGAGGCAGG
  GreenII (625) AAGGTTAAGCTGTATGAGCATGCCGAAGCTCATTCTGGGCTGCCGAGGCAGG
Consensus (625) AAGGTTAAGCTGTATGAGCATGCCGAAGCTCATTCTGGGCTGCCGAGGCAGG
                                                                            Section 14
         (677) 677    684
   GreenI (677) CCAAGTAA
  GreenII (677) CCAAGTAA
Consensus (677) CCAAGTAA
```

FIG. 7

```
                                                                          Section 1
              (1)  1          10         20         30         40        52
Greenlaa     (1) MSVIKPDMKIKLRMEGAVNGHKFVIEGDGKGKPFEGKQTMDLTVIEGAPLPF
GreenIIaa    (1) MSVIKPDMKIKLRMEGAVNGHKFVIEGDGKGKPFEGKQTMDLTVIEGAPLPF
Consensus    (1) MSVIKPDMKIKLRMEGAVNGHKFVIEGDGKGKPFEGKQTMDLTVIEGAPLPF
                                                                          Section 2
             (53) 53         60        70         80         90        104
Greenlaa    (53) AYDILTTVFDYGNRVFAKYPKDIPDYFKQTFPEGYSWERSMTYEDQGICIAT
GreenIIaa   (53) AYDILTTVFDYGNRVFAKYPKDIPDYFKQTFPEGYSWERSMTYEDQGICIAT
Consensus   (53) AYDILTTVFDYGNRVFAKYPKDIPDYFKQTFPEGYSWERSMTYEDQGICIAT
                                                                          Section 3
            (105) 105   110        120        130        140          156
Greenlaa  (105) NDITMMKGVDDCFVYKIRFDGVNFPANGPVMQRKTLKWEPSTEKMYVRDGVL
GreenIIaa (105) NDITMMKGVDDCFVYKIRFDGVNFPANGPVMQRKTLKWEPSTEKMYVRDGVL
Consensus (105) NDITMMKGVDDCFVYKIRFDGVNFPANGPVMQRKTLKWEPSTEKMYVRDGVL
                                                                          Section 4
            (157) 157        170        180        190              208
Greenlaa  (157) KGDVNMALLLEGGGHYRCDSKTTYKAKKVVQLPDYHFVDHRIEIVSHDKDYN
GreenIIaa (157) KGDVNMALLLEGGGHYRCDFKTTYKAKKVVQLPDYHFVDHRIEIVSHDKDYN
Consensus (157) KGDVNMALLLEGGGHYRCD KTTYKAKKVVQLPDYHFVDHRIEIVSHDKDYN
                                                                          Section 5
            (209) 209             227
Greenlaa  (209) KVKLYEHAEAHSGLPRQAK
GreenIIaa (209) KVKLYEHAEAHSGLPRQAK
Consensus (209) KVKLYEHAEAHSGLPRQAK
```

FLUORESCENT PROTEINS FROM AQUATIC SPECIES

CROSS-REFERENCE TO RELATED APPLICATION

This application is a divisional of U.S. patent application Ser. No. 10/314,936, filed Dec. 9, 2002, which is incorporated herein by reference in its entirety.

REFERENCE TO GOVERNMENT GRANT

This invention was made with United States government support awarded by the National Institute of Environmental Health Sciences-MFBSC, Contract # ES05705, NIH-National Institute of Neurological Disorders and Stroke, Contract # NS36998, and National Institute of General Medicine, Contract # GM 57505. The United States has certain rights in this invention.

BIBLIOGRAPHY

Complete bibliographic citations of the references referred to herein by the first author's last name in parentheses can be found in the Bibliography section, immediately preceding the claims.

FIELD OF THE INVENTION

The invention relates to the field of biochemical assays and reagents. More specifically, this invention relates to fluorescent proteins and to methods for their use.

DESCRIPTION OF THE RELATED ART

The number of available fluorescent reporter genes has increased as researchers have isolated genes encoding fluorescent proteins from an increasing variety of organisms and included the genes in cloning cassettes. For example, fluorescent proteins from sea creatures have been used as reporter genes capable of integration into DNA via cloning cassettes. Products of these genes fluoresce under certain wavelengths of light, permitting the tracking of proteins in, e.g., heterologous cells, such as dog and monkey cells. The most commonly used proteins of this nature fluoresce green, and were obtained from the jellyfish, *Aequorea victoria*, and sea pansy, *Renilla reniformis*. Additionally, a red fluorescent protein (RFP), known as drFP583, and a turquoise fluorescent protein, known as dsFP483, have been isolated from the IndoPacific mushroom corals (*Discosoma* sp. "red" and *Discosoma striata*, respectively). Both *Discosoma* and *Actinodiscus* are mushroom corals, soft bodied anthozoans that do not produce an external skeleton. It should be noted that the relationship between the genus *Discosoma* and the genus *Actinodiscus* is not well understood. Both *Actinodiscus* and *Discosoma* are members of the Actinodiscidae Family, which is a member of the Corallimporpharia (mushroom) Order. The taxonomy of the Corallimporpharia is poorly defined, and therefore, the nature of the relation of *Actinodiscus* to *Discosoma* is uncertain. *Discosoma* and *Actinodiscus* are believed to be different genera of the same family, but they could be more closely or distantly related.

The availability of a variety of fluorescent proteins and reagents has enhanced the opportunities for researchers employing reporter proteins in their work. Isolated DNAs encoding fluorescent proteins have been mutated to alter their optical properties. For instance, mutating tyrosine at amino acid 66 to histidine in the amino acid composition of the *Aequorea* green fluorescent protein (GFP) changes this protein to one that fluoresces blue. Changing amino acid 64 from phenylalanine to leucine, amino acid 65 from serine to threonine, and amino acid 145 from tyrosine to phenylalanine generates a GFP that fluoresces at a brighter intensity than the parent molecule and has a shifted excitation optima. In addition, by genetically modifying the amino acid composition of GFP, researchers have been able to change its light absorption/emission characteristics, creating yellow fluorescent proteins.

Fluorescent proteins can be used in a number of assays. In one example, fluorescent proteins can be used in Fluorescence Resonance Energy Transfer (FRET) assays. FRET occurs with fluorophores for which the emission spectrum of one overlaps with the excitation spectrum of the second. When the fluorophores are brought into close proximity, excitation of the "donor" results in emission from the "acceptor." Pairs of such fluorophores are thus useful for monitoring molecular interactions. Fluorescent proteins, such as GFP, are useful for analysis of protein:protein interactions either in vivo or in vitro if their fluorescent emission and excitation spectra overlap to allow FRET. The donor and acceptor fluorescent proteins may be produced as fusion proteins with the proteins being analyzed for interactions. These types of applications of GFPs are particularly appealing for high throughput assays, because the readout is direct and independent of subcellular localization.

Because of its easily detectable green fluorescence, GFP from *Aequorea* has been used widely to study gene expression and protein localization. Furthermore, GFP, like other fluorescent proteins, does not require a substrate or cofactor to fluoresce; hence, it is possible to directly express GFP and use it as a reporter in numerous species and in a wide variety of cells. However, factors other than fluorescence color and intensity affect the utility of a protein in research. The stability of many fluorescent proteins makes them undesirable reporters to use if one seeks to determine short term or repetitive events. Moreover, accumulated protein can be toxic to some mammalian cells. For example, certain forms of GFP from *Aequorea* have been demonstrated to induce apoptosis (Liu, et al.). Although the inventors do not wish to be limited to a single explanation of the toxicity of GFP from *Aequorea*, it is believed that this is probably due to free radical ($H_2O_2$) formation which occurs in a 1:1 stoichiometry with GFP production, making high levels of GFP expression particularly toxic. This is believed to be a direct result of chromaphore maturation and is believed to occur in every known GFP.

Photobleaching is another concern with previous fluorescent proteins. Photobleaching is a light induced change in a fluorophore, resulting in the loss of absorption of light of a particular wavelength by the fluorophore. This results in loss of fluorescence of the fluorophore. Many fluorescent proteins rapidly photobleach under excitation. This process is usually reversible but can limit the usefulness of GFP expression, e.g. by reducing time available to photograph specimens. However, where the photobleaching is rapidly reversible, this property makes the fluorescent protein useful for certain applications.

Thus, the need remains for easily expressible fluorescent proteins that have a range of spectral outputs and low toxicity to maximize research capabilities. Such research applications include, but are not limited to, short-lived fluorescent proteins as genetic reporters, which would enable monitoring of short-lived activities. Such research applications further include, but are not limited to, low toxicity fluorescent proteins that would allow long-term monitoring or stable transfection of cells or organisms.

Furthermore, the need also remains for fluorescent proteins having novel emission spectra. This would permit monitoring multiple processes simultaneously and could minimize background fluorescence. It would also increase the choices available for FRET analysis systems. Moreover, fluorescent proteins having brighter relative fluorescence are needed to permit detection of low level expression of the fluorescent proteins.

SUMMARY OF THE INVENTION

The invention, which is defined by the claims set out at the end of this disclosure, is intended to solve at least some of the problems noted above. The invention provides improved fluorescent proteins with enhanced properties e.g., substantially enhanced fluorescence and reduced toxicity. The improved fluorescent proteins are useful in research and can be used, e.g., to determine or detect gene expression, e.g., up- or down-regulation, to monitor promoter activity, to allow longer term monitoring, and to localize proteins.

A new, wild-type red fluorescent protein (RFP) was isolated from an aquatic species believed to be either an *Actinodiscus* or *Discosoma* species. This protein is referred to hereinafter as Ac/DsRFP. The invention provides two protein mutants derived from Ac/DsRFP. The mutant RFPs of the invention are referred to herein as Red I and Red II. An isolated nucleic acid encoding each of these and their associated amino acid sequences are also included.

In addition, a novel green fluorescent protein (GFP) was isolated from *Montastraea cavernosa*. This protein is referred to herein as McGFP. The invention provides two novel proteins derived from McGFP. Preferred novel proteins are referred to herein as Green I and Green II. It was also discovered that certain mutants of McGFP photobleach very quickly.

The invention also provides a nucleic acid construct that includes a first coding sequence that encodes a selected polypeptide and a second coding sequence that encodes a fluorescent protein of the invention. The first coding sequence is fused to the second coding sequence such that expression of the fused sequence yields a fluorescent hybrid protein in which the polypeptide encoded by the first coding sequence is fused to the polypeptide encoded by the second coding sequence.

Vectors including the various isolated nucleic acids of the invention are also provided. Vectors of varying capacities are well known to molecular biologists and can be used to transform a eukaryotic or prokaryotic cell. They can also be used with in vivo and in vitro expression systems.

A method of detecting expression of a nucleic acid encoding a fluorescent protein is also provided. The method includes introducing the nucleic acid of the invention into a cell or organism. In a preferred embodiment, a promoter controls expression of the nucleic acid. Expression of the nucleic acid is detected by emission of fluorescent light, allowing detection of expression of the nucleic acid. In a preferred embodiment, the cell is a eukaryotic cell. In another preferred embodiment, the cell is a prokaryotic cell. The expression of the nucleic acid can be detected in vivo. It can also be detected in vitro and in fixed cells, such as formalin fixed cells.

In a preferred embodiment of the method of detecting expression of a nucleic acid, a gene of interest is fused to nucleic acid encoding a fluorescent protein. The fusion protein may include a subcellular specific locator signal, allowing measurement of expression from the promotor and/or subcellular localization. Expression of the gene of interest is detected by emission of fluorescent light.

Also provided is a cell including a nucleic acid of the invention. In a preferred embodiment, the nucleic acid is integrated into a genome of the cell. In another preferred embodiment, the nucleic acid is not integrated into a genome of the cell. For example, the nucleic acid can exist extrachromosomally.

An animal having an isolated nucleic acid of the invention is additionally provided. In a preferred embodiment, the animal is a zebrafish.

BRIEF DESCRIPTION OF THE DRAWINGS

Preferred exemplary embodiments of the invention are illustrated in the accompanying drawings in which:

FIGS. 1A-1B are a sequence alignment of the DNA encoding two mutant red fluorescent proteins: Red I (SEQ ID NO:1) and Red II (SEQ ID NO: 3), each of which was generated from a protein originally isolated from *Actinodiscus/Discosoma* sp. In this and all other alignments, the differences between the sequences being aligned are indicated by a missing monomer in the "consensus" line.

FIG. 2 is an alignment of the amino acids encoded by the DNA sequences of Red I (SEQ ID NO: 2) and Red II (SEQ ID NO: 4).

FIGS. 6A-6B show a sequence alignment of the DNA encoding two mutant green fluorescent proteins: Green I (SEQ ID NO:5) and Green II (SEQ ID NO:7), each of which was generated from a protein originally isolated from *M. cavernosa*.

FIG. 7 is an amino acid alignment of the amino acids encoded by the DNA sequences of Green I (SEQ. ID. NO: 6) and Green II (SEQ. ID. NO:8).

Figure 3:
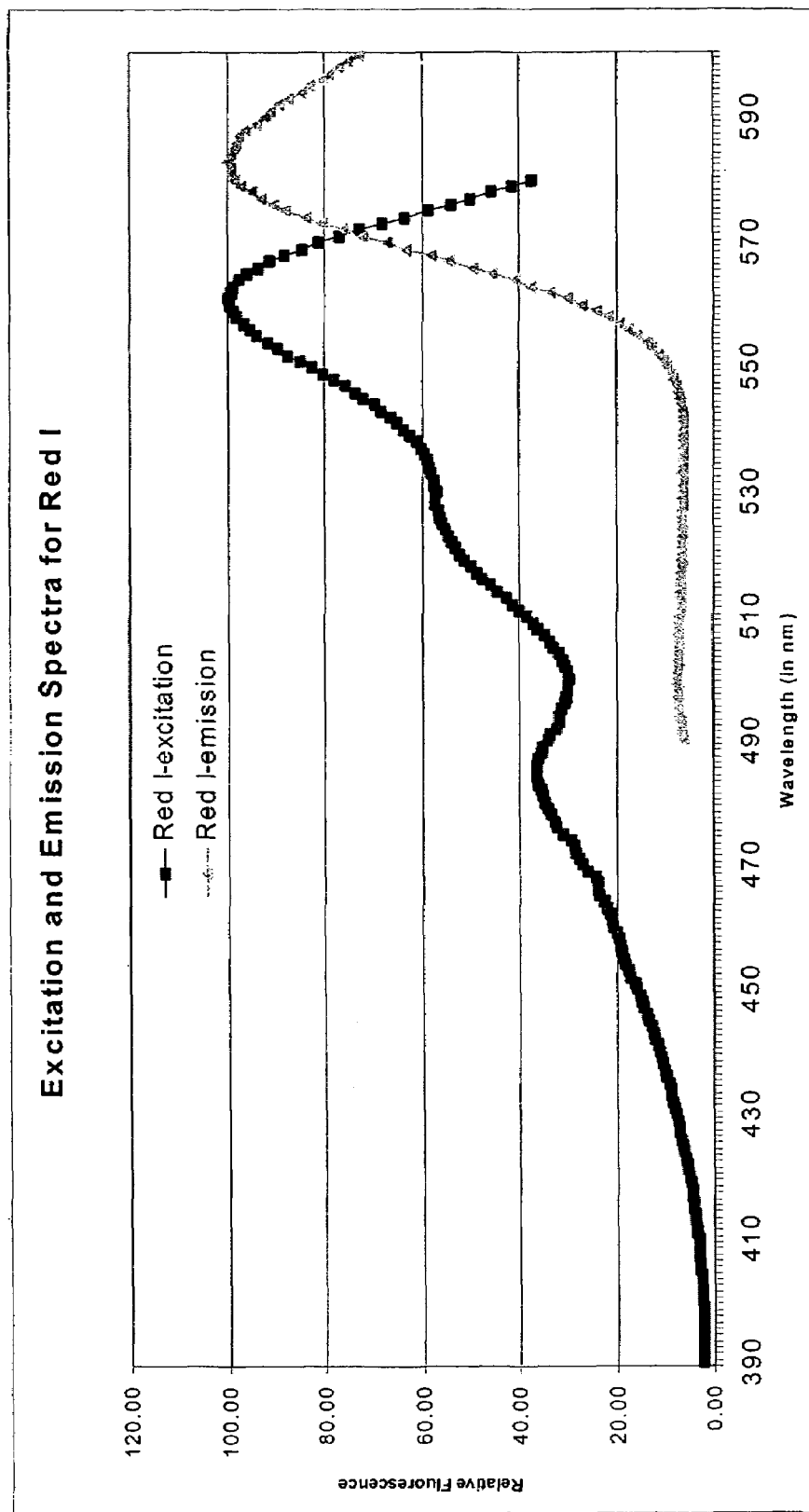
FIG. 3 is a graph of a spectral analysis of Red I.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

Definitions:

For purposes of the present invention, the following definitions apply:

The standard, one-letter codes "A," "C," "G," "T," and "U" are used herein for the nucleotides adenine, cytosine, guanine, thymine, and uracil, respectively. "N" designates any nucleotide. Oligonucleotide or polynucleotide sequences are written from the 5'-end to the 3'-end.

As used herein, "amino acids" are described in keeping with standard polypeptide nomenclature, J. Biol. Chem., 243:3557-59, (1969). All amino acid residues identified herein are in the natural L-configuration. In keeping with standard polypeptide nomenclature, abbreviations for amino acid residues are as shown in the following Table of Correspondence.

TABLE OF CORRESPONDENCE

| 1-Letter | 3-Letter | AMINO ACID |
|---|---|---|
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

By "protein" and "polypeptide" is meant any chain of amino acids, regardless of length or post-translational modification, e.g., glycosylation or phosphorylation. The synthetic genes of the invention may also encode a variant of a naturally-occurring protein or polypeptide fragment thereof. Preferably, such a protein polypeptide has an amino acid sequence that is at least 85%, preferably 90%, and most preferably 95% or 99% identical to the amino acid sequence of the naturally-occurring (native) protein from which it is derived.

The term "isolated" when used in relation to a nucleic acid, as in "isolated nucleic acid" or "isolated polynucleotide," refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids, e.g., DNA and RNA, are found in the state they exist in nature. For example, a given DNA sequence, e.g., a gene, is found on the host cell chromosome in proximity to neighboring genes; RNA sequences, e.g., a specific mRNA sequence encoding a specific protein, are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid may be present in single-stranded or double-stranded form. When an isolated nucleic acid is to be utilized to express a protein, the oligonucleotide contains at a minimum, the sense or coding strand, i.e., the oligonucleotide may be single-stranded, but may contain both the sense and anti-sense strands, i.e., the oligonucleotide may be double-stranded.

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides, e.g., proteins and enzymes, are found in the state in which they exist in nature.

The term "purified" or "to purify" means the result of any process that removes some of a contaminant from the component of interest, such as a protein or nucleic acid. The percent of a purified component is thereby increased in the sample.

With reference to nucleic acids of the invention, the term "nucleic acid" refers to DNA, genomic DNA, cDNA, RNA, mRNA and a hybrid of the various nucleic acids listed. The nucleic acid can be of synthetic origin or natural origin. A nucleic acid, as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties, i.e., altered characteristics, when compared to the wild-type gene or gene product. It is noted that naturally-occurring mutants can be isolated; these are identified by the fact that they have altered characteristics when compared to the wild-type gene or gene product.

As used herein, "higher relative fluorescence intensity" or "increased brightness" refers to fluorescence intensity or brightness that is greater than that exhibited by a wild-type fluorescent protein under a given set of conditions. Generally, an increase in fluorescence intensity or brightness means that fluorescence of a variant is at least 25% or more, and preferably greater than 50%, or more, and more preferably greater than 100% or more intense or bright than the wild-type fluorescent protein under a given set of conditions.

The term "nucleic acid construct" denotes a nucleic acid that is composed of two or more nucleic acid sequences that are derived from different sources and that are ligated together using methods known in the art.

The term "host cell" as used herein, refers to a cell from any organism. Preferred host cells are derived from plants, bacteria, yeast, fungi, insects, or other animals. Methods for introducing polynucleotide sequences into various types of host cells are well known in the art. Host cell includes progeny or potential progeny of these designations.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The term "expression vector" as used herein refer to DNA or RNA sequences containing a desired coding sequence and appropriate DNA or RNA sequences necessary for the expression of the operably linked coding sequence in a particular host organism. Prokaryotic expression vectors typically include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors typically include a promoter, optionally a polyadenlyation signal and optionally an enhancer sequence.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements, e.g., promoters, enhancers, and termination elements, in an expression vector.

In the present invention, there may be employed conventional molecular biology and microbiology within the skill of the art. Such techniques are explained fully in the literature. See, e.g., Sambrook, Fritsch & Maniatis, Molecular Cloning: A Laboratory Manual, Third Edition (2001) Cold Spring Harbor Laboratory Press, Cold Spring Harbor, N.Y.

In accordance with the invention, new wild-type fluorescent proteins have been isolated. The wild-type fluorescent proteins have been mutated to create mutant forms of the fluorescent proteins that have, e.g., a higher relative fluorescence intensity or a greater ability to resist photobleaching than their respective wild-type fluorescent proteins.

I. Isolation of Wild-type Fluorescent Proteins

Briefly, tissue from an organism of interest was collected and homogenized by methods described in detail below. RNA was isolated, and RT-PCR was performed. Size-selected DNA was recovered from an agarose gel, and then ligated into a vector suitable for bacterial selection. The vector can include an inducible or constitutive promoter. In a preferred embodiment, plasmids were used as the vectors. Plasmids were electroporated into competent bacteria. Bacteria were incubated on LB-ampicillin plates (100 µg/ml). Clones of interest were isolated based upon qualitative determination of fluorescence intensity and/or color quality.

Using this procedure, which is explained in detail in the Examples below, a cDNA encoding a wild-type red fluorescent protein was isolated from an aquatic species believed to be *Actinodiscus* or *Discosoma*. Because of the uncertainty in the relationship of the genera *Actinodiscus* or *Discosoma*, which is discussed above in the Description of the Related Art section, this protein is referred to hereinafter as Ac/DsRFP. The isolated cDNA encoding Ac/DsRFP was further mutated, and isolates were selected based upon properties of interest, as is detailed below. Additionally, using the methods described herein, a cDNA encoding a wild-type green fluorescent protein (GFP) was isolated from *Montastraea cavernosa* and is referred to herein as McGFP. As is described below, the isolated cDNA encoding McGFP was further mutated, and selected based upon properties of interest.

II. Creation of Mutated Fluorescent Proteins

For each of the wild-type genes isolated, random mutations in the coding sequences were induced in each through PCR conducted under low stringency conditions (low annealing temperature, excessively long extension times, extra cycles, as described below) to induce mutations during the polymerization. The resulting PCR products were cloned into bacterial expression vectors. Clones were screened for increased relative fluorescence, colors of interest, and decreased photobleaching when compared to the corresponding wild-type fluorescent protein. The vector DNA was then purified from selected clones and sequenced to determine the relevant PCR-induced mutational changes. This process was then reiterated several times.

a. Red I and Red II

The DNA encoding the Ac/DsRFP, the wild-type RFP from *Discosoma*, was mutated as indicated above with several rounds of low stringency PCR. After cloning into a vector and visual screening of transformed bacteria for fluorescent properties, the proteins encoded by Red I and Red II were selected based upon higher relative fluorescence intensity when compared to the parent Ac/DsRFP wild type. Red II has a fluorescent intensity that is at least 50% greater than the intensity of Red I, as determined qualitatively.

The DNA sequences of Red I (SEQ ID NO:1) and Red II (SEQ ID NO:2) are shown in FIGS. 1A-1B. Compared to the DNA encoding Red I, the DNA encoding Red II contains a single nucleotide difference: at position 694: Red I has a G, and Red II has an A. The amino acid sequences of Red I (SEQ ID NO:2) and Red II (SEQ ID NO:4) are shown in FIG. 2. This figure indicates that at position 232, Red I has a D, whereas Red II has an N.

Figure 4:
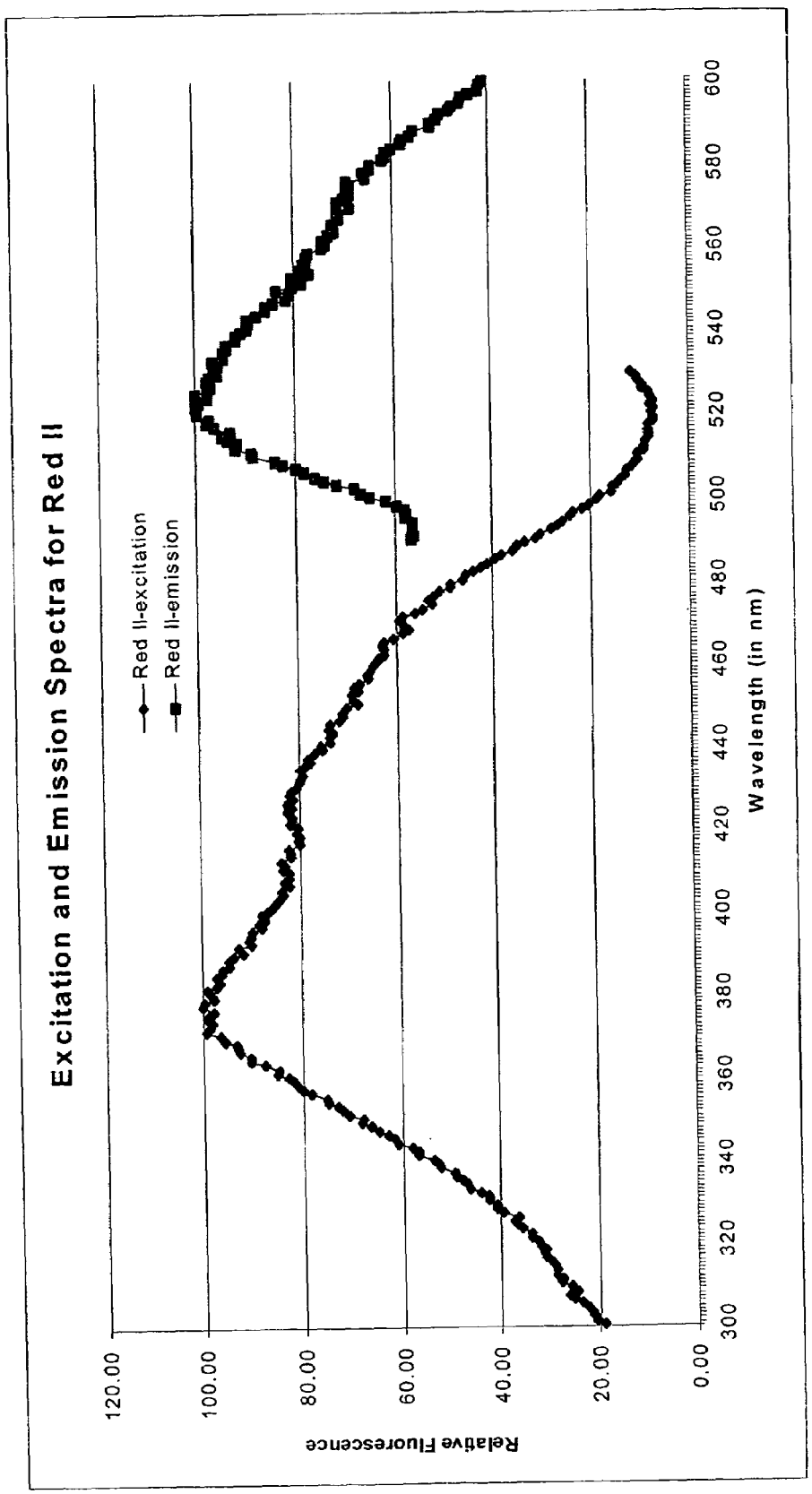
FIG. 4 is a graph of a spectral analysis of Red II.
Figure 5:
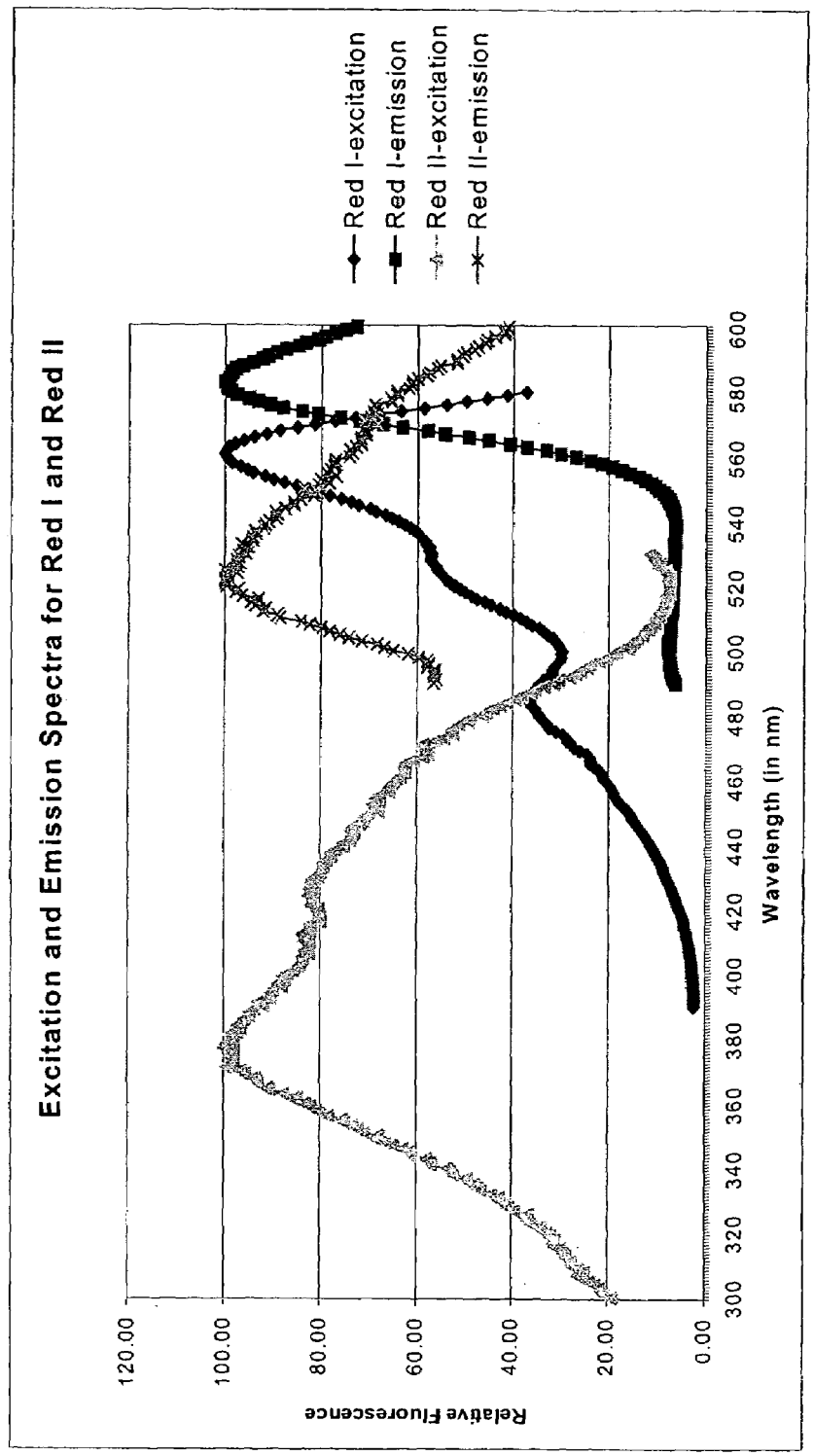
FIG. 5 is a graph of spectral analyses of Red I and Red II.

Referring now to FIG. 3-5, spectral analyses of Red I and Red II and for both Red I and Red II are shown.

b. Green I and Green II

The DNA sequence encoding, McGFP, the wild-type GFP from *M. cavernosa*, was mutated using PCR under low stringency conditions, as described herein. A mutant GFP with brighter fluorescence was isolated and is indicated as Green I. A second round of low stringency PCR was performed on Green I, yielding a second mutant GFP with high resistance to photobleaching and is indicated as Green II. When compared to the DNA sequence encoding the Green I, the DNA encoding Green II contains a single nucleotide change: a cytosine to thymine mutation at nucleotide 527, as shown in FIGS. 6A-6B as SEQ ID NO:5 and SEQ ID NO:7.

The amino acid sequences are shown in FIG. 7 as SEQ ID NO6 and SEQ ID NO:8. This figure indicates an S at position 176 in Green I, and an F at the same position in Green II.

Green I had higher relative fluorescence intensity when compared to the McGFP. Green II also had higher relative fluorescence but also has a high resistance to photobleaching, a property not evident in the Green I protein. Using a mercury arc laser commonly employed in fluorescence microscopy, manipulated by an ATTOARC™ HBO 100 W variable power supply, Green I was found to photobleach under appropriate conditions. Low laser intensity is considered to be less than 25% intensity, and high laser intensity is considered to be greater than 75% for this instrument. Cells were visualized using a ZEISS® AXIOVERT® S100 Microscope. Under low laser intensity, such as 10%, both derivative proteins appear the same. However, after several seconds under high laser intensity, such as 80%, Green I light is not visible. After several minutes in the dark followed by re-illumination, the fluorescence of Green I is again evident. Green I is also unusual in that excitation with 420 mm light rapidly reverses photobleaching. Green II does not undergo this photobleaching response.

Figure 8:
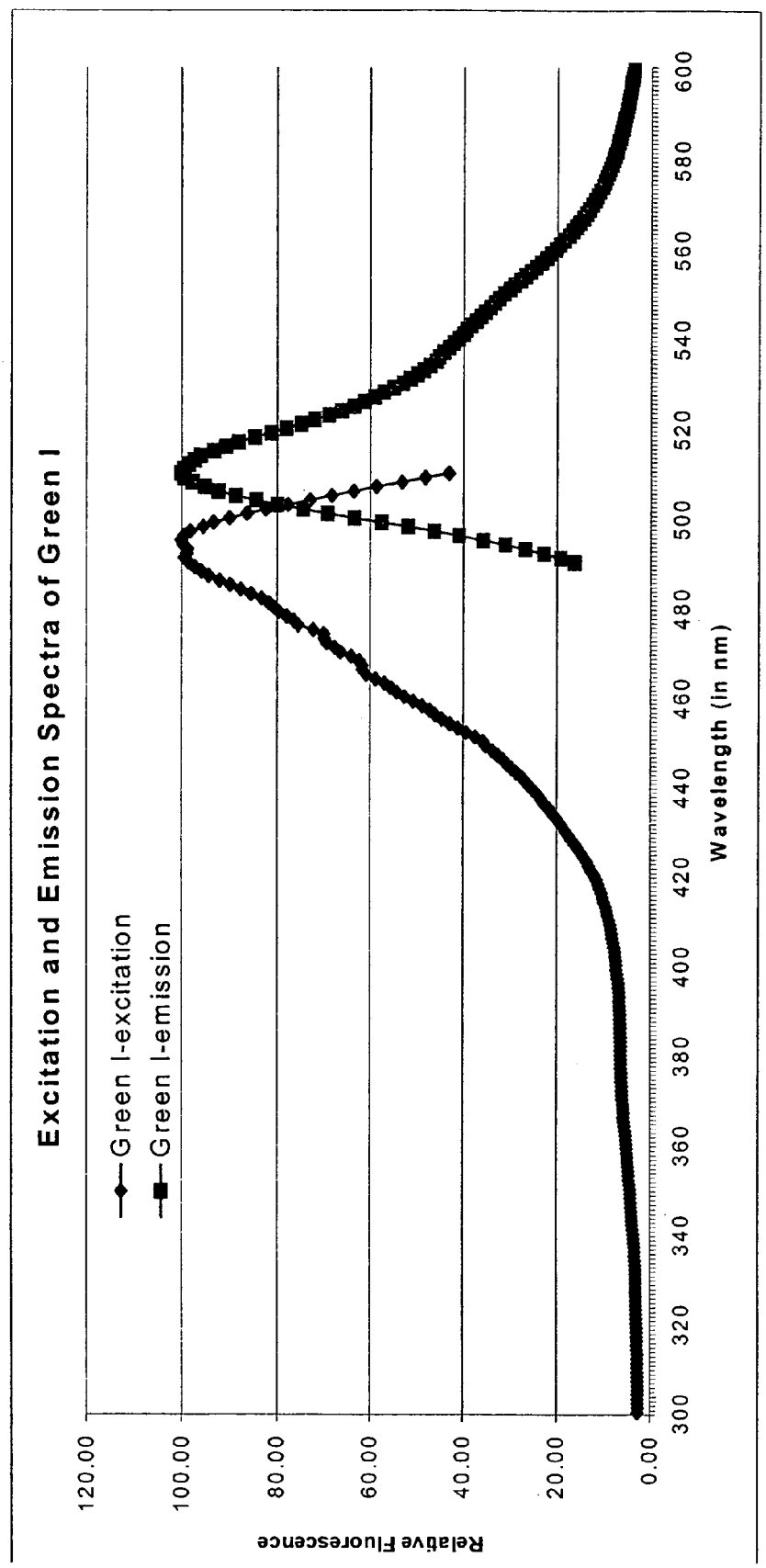
FIG. 8 is a graph of a spectral analysis of Green I.
Figure 9:
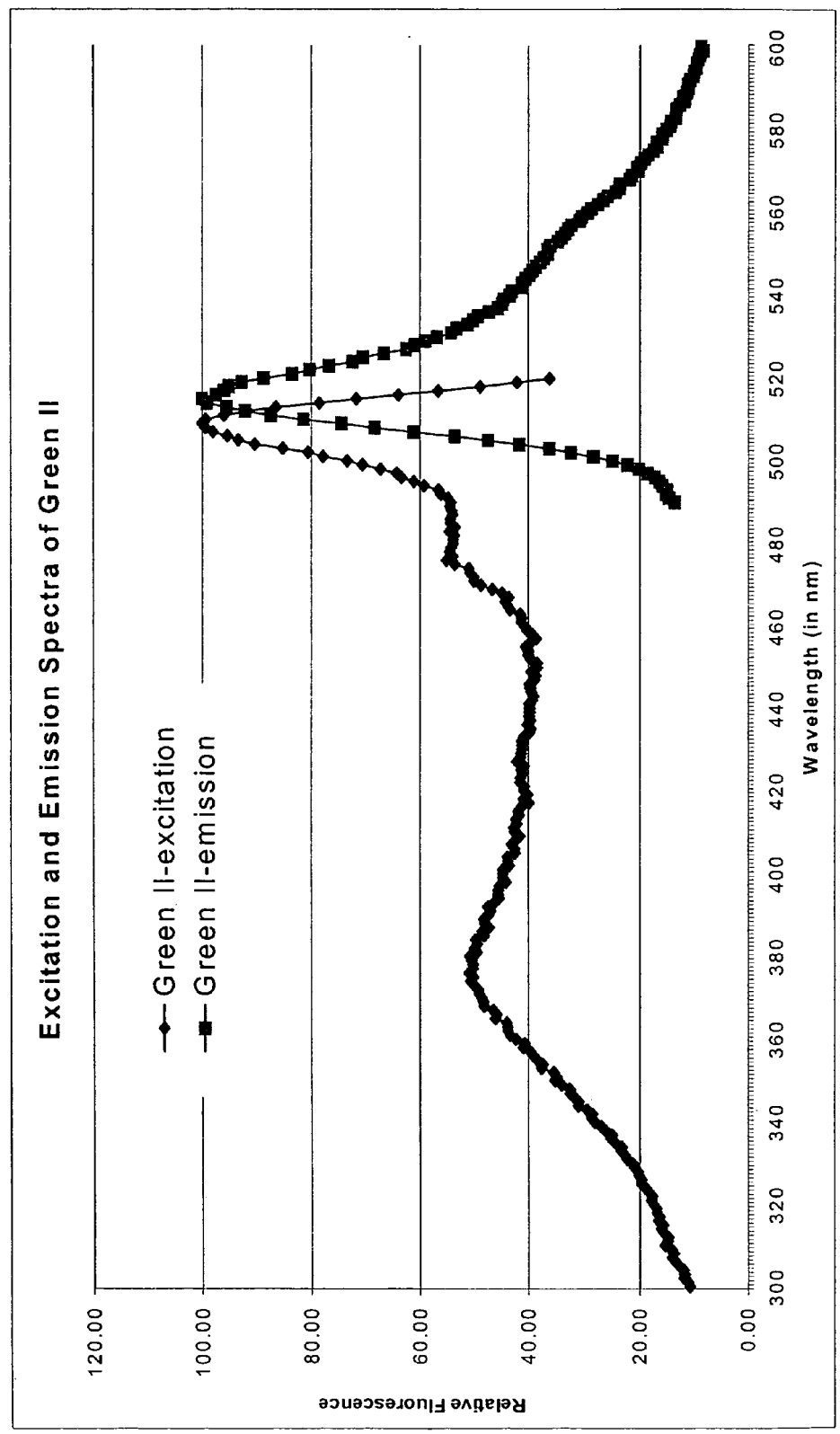
FIG. 9 is a graph of a spectral analysis of Green II.
Figure 10:
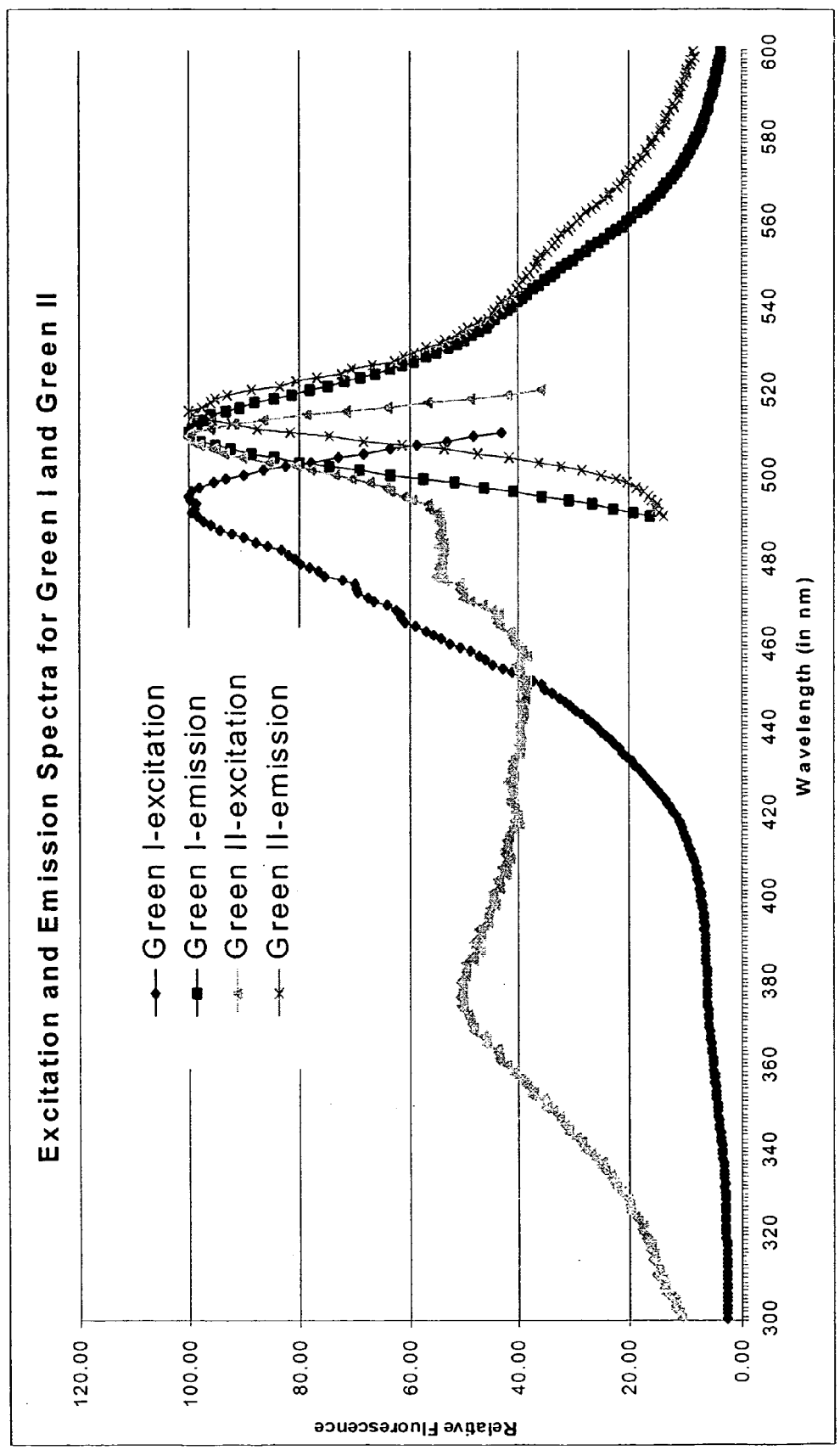
FIG. 10 is a graph of spectral analyses of Green I and Green II.

Referring to FIGS. 8-10, spectral analyses of Green I (FIG. 8) and Green II (FIG. 9) and for both Green I and Green II (FIG. 10) are shown.

IV. Exemplary Uses of the Fluorescent Proteins

All of the fluorescent proteins described herein can be used as markers to detect expression of a gene of interest such as by inserting the gene of interest and DNA encoding a fluorescent protein into a vector. The vector can be transformed into a eukaryotic or prokaryotic host cells, such as, e.g., bacterial cells, insect cells, yeast cells, and mammalian cells. As is known in the art, host cells are competent or can be rendered competent by a variety of techniques, including, but not limited to, calcium phosphate precipitation, fusion of the recipient cells with bacterial protoplasts containing the DNA, treatment of the recipient cells with liposomes containing the DNA, DEAE dextran, receptor-mediated endocytosis, electroporation, and micro-injection of the DNA directly into the cells. The DNA can be integrated into the chromosomal DNA of the host cell or it can exist extrachromosally, such as via a plasmid.

Fluorescent proteins of the invention can also be used in biochemical assays and as reagents. For example, the fluorescent proteins can be used as a reporter to monitor fermentation processes and to quantify gene expression.

Additionally, the fluorescent proteins of the invention provide additional fluorescent proteins that can be used in multiple labeling systems. For example, one of the GFPs of the invention can be used to label a first population of cells and one of the RFPs of the invention can be used to label a second population of cells such that two different populations of cells can be tracked, e.g., during fluorescence activated cell sorting. Similarly, Red I and Red II can be used, e.g., to label and track different populations of cells because Red I and Red II fluoresce at different wavelengths.

Further, the inventive fluorescent proteins can also be used in prokaryotic and eukaryotic expression systems. For instance, fusion proteins can be generated to contain coding sequences for a fluorescent protein and another gene. A typical fusion protein of the invention includes a first coding sequence that encodes a selected polypeptide and a second coding sequence that encodes a fluorescent protein of the invention. The first coding sequence is fused to the second coding sequence such that expression of the fused sequence yields a fluorescent hybrid protein in which the polypeptide encoded by the first coding sequence is fused to the polypeptide encoded by the second coding sequence. It is believed that the fluorescent proteins of the invention can be fused either at the 3' or 5' end of the coding sequence. Furthermore, unlike fusion proteins with coding sequences for proteins such as β-galactosidase, fusion proteins containing coding sequences for a fluorescent protein do not require exogenously added substrates or cofactors. This beneficially permits the fluorescent proteins to be used in living cells.

The fluorescent proteins provided herein can also be used as in vivo markers, such as in mRNA microinjection assays. Other examples of uses of fluorescent proteins are as an in vivo marker in transgenic mice, *Caenhorbabditis elegans*, *Drosophila melanogaster*, and Zebrafish.

In addition, fluorescent proteins of the invention can be used as taxonomic markers for studies of cnidarian genetics, color indicators in diagnostic kits, colored food additives, and cosmetic ingredients.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Species Collection and Animal Husbandry

Coral colonies were obtained from two sources. First, a solid, brick-red colony consisting of several *Actinodiscus/Discosoma* sp. polyps was obtained from a local aquarium store. Second, *Montastraea cavernosa* colonies were collected from reefs in the South Florida area. Both species were maintained in small aquariums with flow-through, filtered sea water.

Example 2

Isolation of Total RNA, Reverse Transcription, Amplification and Recovery of cDNAs RNA was isolated using the TOTALLY RNA™ kit (Catalog # 1902, Ambion, Inc., Austin, Tex.) from a single polyp (*Actinodiscus/Discosoma* sp.) or from a cellular mass lightly airbrushed from the underlying skeleton (*M. cavernosa*). Briefly, the tissue was homogenized and mixed by tube inversion with approximately 10 volumes of denaturation solution and extracted with 1 volume of phenol/chloroform. The aqueous supernatant was transferred to a clean vessel. One-tenth volume of 3M sodium acetate was added to the supernatant, which was then extracted an additional time with 1 volume of acid-phenol/chloroform. Again, the aqueus supernatant was transferred to a clean vessel. One volume of isopropanol was added to the supernatant, and total RNA was precipitated by centrifugation. The pellet was washed with 75% ethanol and resuspended in 50 uL RNAse-free water. Yield was measured with a spectrophotometer, and quality was assesed by gel electrophoresis.

The RNA thus isolated was used in a FIRSTCHOICE® RLM-RACE$^{SM}$ kit (catalog # 1700, Ambion, Inc.) to create and amplify cDNAs. The "small reaction" protocol, as per RLM-RACE™ protocol version 0010, was followed. Briefly, total RNA is treated with Calf intestinal phosphatase (CIP) to remove 5' phosphates from degraded and non-capped RNA, and then phenol:chloroform extracted. Tobacco acid pyrophosphatase (TAP) was then used to remove the cap from full-length mRNA. An included 5' RACE adaptor (5'-GCUGAUGGCGAUGAAUGAA-CACUGCGUUUGCUGGCUUUGAUGAAA-3') (SEQ ID NO:9) was ligated to total decapped mRNAs with T4 RNA ligase. Reverse transcription was accomplished using MMLV reverse transcriptase and a polyT primer (5'-CTC-GAGAAGCTTGAATTCGGATC-CTTTTTTTTTTTTTTTTTT-3') (SEQ ID NO: 10).

Amplification of the resultant cDNA was done using the same polyT primer, the 5' RACE™ Outer Primer (5'-GCT-GATGGCGATGAATGAACACTG-3') (SEQ ID NO:11) and SUPERTAQ™ Polymerase (Ambion, Inc., catalog 2050).

PCR was conducted as follows: 94° C./5 min, 80° C. hold, add polymerase, 34 cycles of 94° C./30 sec, 60° C./1 min, 72° C./1 min and a final 10 min of 72° C. Amplified cDNAs were gel purified. The fraction from about 500-1200 base pair (bp) was collected and recovered by slow speed centrifugation through siliconized glass wool followed by isopropanol precipitation.

Example 3

Transformation and Selection of Bacterial clones, Plasmid Preparation, and DNA Sequencing of Wild-type Fluorescent Proteins The gel purified cDNA fraction was ligated into the pCR II cloning vector (Invitrogen, Carlsbad, Calif.), with resultant plasmids electrotransformed into Top 10 *E. coil* (Invitrogen). Transformed bacteria were grown on LB-ampicillin (100 μg/ml) plates and colonies were screened for fluorescence using a LEICA® MZFLIII fluorescence stereo dissection microscope. Single fluorescent colonies were picked, restreaked for several rounds to resolve mosaicism, and grown in liquid culture. Plasmid DNA was prepared using the QIAGEN® Midi kit (Qiagen, Valencia, Calif.).

A colony expressing a wild-type red fluorescent protein (RFP) was isolated from the bacterial colonies generated from the *Actinodiscus/Discosoma* sp. 1 RNA. This is herein referred to as *Ac/Ds*RFP.

In addition, a colony expressing a wild-type green fluorescent protein (GFP) was isolated from the bacterial colonies generated from the *M. cavernosa* RNA and was named *Mc*GFP.

Example 4

Generation of Mutations of Fluorescent Proteins

Each of the genes coding for the wild-type proteins was subject to error-prone PCR. The PCR products were cloned, and were selected qualitatively based on expression of proteins encoded by the PCR products.

Specifically, a 5' "upper" primer containing a Kpn I restriction site, Shine-Dalgarno and Kozak consensus uptranslation sequences, the staffing ATG of the coding region, and approximately 10 bp of downstream homology was designed for both *Ac/Ds*RFP and *Mc*GFP. The upper primer for *Ac/Ds*RFP was: 5'-CCGGTACCTAAGGAGGC-CACCATGAGTTGTTCC-3' (SEQ ID NO:12) and the upper primer for *Mc*GPP was: 5'-CCGGTACCTAAGGAG-GCCACCATGAGTGTGATAAAAC-3' (SEQ ID NO:13)

A 3' "lower" primer containing an Xba I restriction site, the stop codon of the coding region, and approximately 10 bp of upstream homology was also designed for each of the fluorescent protein isolates. The lower primer for *Ac/Ds*RFP was:

5'-CCACTAGTCTAGATCATTACCGCTC-3' (SEQ ID NO:14) and the lower primer for *Mc*GFP was:

5'-GGTCTAGATTACTTGGCCTGCCTC-3' (SEQ ID NO:15).

Low-stringency PCR protocol was performed on the fluorescent protein plasmid DNA using the above primers. The conditions were: 94° C./5 min, 80° C./hold, add polymerase, 10 cycles of 94° C./1 min, 42° C./2 min, 72° C./3 min, 30 cycles of 94° C./30 sec, 55° C./1min. 72° C./1 min and a final 10 min of 72° C. The PCR products were purified with a phenol/chloroform extraction and isopropanol precipitation, digested with Kpn I/Xba I, gel purified, and ligated into Kpn I/Xba I digested pBS II KS+ plasmid (Stratagene, La Jolla, Calif.). The ligation mix was electrotransformed into Top 10 cells (Invitrogen) and colonies were screened for 1) brightness greater than parent, 2) speed of color development, 3) size, and 4) color.

Two mutants were generated from *Ac/Ds*RFP, the wild-type red fluorescent protein by several rounds of low stringency PCR, as described above. After cloning into a vector and visual screening of transformed bacteria for fluorescent properties, the proteins encoded by Red I and Red II were selected based upon higher relative fluorescence intensity when compared to the parent *Ac/Ds*RFP wild type. The mutant clones generated were named Red I and Red II.

In addition, the Green I mutant was generated from the *Mc*GFP, the wild-type green fluorescent protein. A second round of low-stringency PCR was performed on the DNA encoding Green I, and colonies meeting the above four criteria were isolated. The mutant clone generated from Green I was named Green II. Sequencing was performed by The University of Iowa DNA Facility (Iowa City, Iowa) using purified plasmid preparations. The DNA sequences of Red I and Red II are shown in FIGS. 1A-1B, and the amino acid sequences are shown in FIG. 2. The DNA sequences of Green I and Green II are shown in FIGS. 6A-6B, and the amino acid sequences are shown in FIG. 7.

Example 5

Fluorescent Proteins Cloned into Other Expression Vectors and Spectral Analysis Thereof For mammalian expression, each of the four mutant fluorescent proteins (Red I, Red II, Green I, and Green II) was restriction digested with KpnI/XbaI, then T4 DNA polymerase treated to create blunt ends, and cloned into pCI-neo Mammalian Expression Vector (Promega, Madison, Wis.) using the blunt end SmaI restriction site to generate pCI-Neo-Red I, pCI-Neo-Red II, pCI-Neo-Green I, and pCI-Neo-Green II.

Spectral analysis was determined on the fluorescent proteins expressed in both mammalian and bacterial cells. Mammalian CHO cells were transfected with pCI-Neo-Red I, pCI-Neo-Red II, pCI-Neo-Green I, or pCI-Neo-Green II plasmid using TRANS-FAST™ Transfection Product (Promega). Spectral analysis was determined on cell lysis of the transfected CHO cells using a SPEX® Fluorolog 1680 0.22 m Double Spectrometer. Red II and Green II plasmids were also expressed in prokaryotic cells. The fragment of the appropriate plasmids was PCR amplified with oligonucleotides that generate NcoI-NotI restriction sites. The PCR ampilcons were digested with NcoI and NotI and cloned into the same sites in a prokaryotic expression vector, which was then used to transform *E. coli* JM109 bacteria. After purification of fluorescent proteins, excitation and emission spectra for some proteins were collected and other proteins were evaluated visually using the ZEISS® microscope. Note that the spectra were recorded at 24 hours, however, mature fluorescence for Red II takes more than 24 hours, and by 48 hours, the emission peak is at 583 nm.

Example 6

Transgenic Animals Expressing the Fluorescent Protein

DNA for microinjection into zebrafish embryos was prepared as described previously (Gibbs et al., 1994), with a final concentration of approximately 2 μg/ml linear DNA and 0.05% phenol red. Under a dissecting microscope, several hundred newly fertilized eggs in embryo rearing solution (ERS—tap water with 25 μl/L neomycin sulfate, 0.5 mg/L methylene blue, 17.5 mg/L sodium thiosulfate, and 125 μl/L Amquel) were placed in a 35 mm petri dish of 1% agar containing a single depression of 1-2 mm. With the left hand, a single egg with an intact chorion was rolled into the depression using a number 5 forceps and held in place with the animal pole upright. With the right hand, the egg was microinjected with a running syringe GILMONT® S-1100 with a 5-10 micron needle tip) into the central lower region of the first cell near the yolk-cytoplasm boundary. Disruption of this boundary and leakage of the DNA solution into the underlying yolk occurred in most eggs and did not harm the resultant embryos. After microinjection, the egg was moved with the left-hand forceps to a 100 mm petri dish containing ERS, and the next egg was rolled into position in the depression. Using this technique 500 or more eggs could be microinjected a day. The average dose per embryo, as established by Southern blot analysis, was 50 pg of DNA. This dose was empirically chosen because it resulted in a high proportion of gene transfer. Under these conditions, approximately half of the embryos died in the first 24 hours, and survival to sexual maturity was expected from 10% to 20% of the eggs injected. However, survival of embryos that were mock injected (received no DNA) was approximately 90% that of controls receiving no treatment.

Living embryos and whole mount tissues from fish were observed and photographed with a LEICA® MZFL III stereo fluorescence dissection microscope equipped with a camera. The filter sets used were an FITC filter set (excitation, 470 nm; emission 515 nm), a modified FITC filter set (LEICA®-GFP) (excitation, 425 nm; emission, 480 nm) or a rhodamine filter set (excitation, 546 nm; emission, 590 nm). Embryos were individually transferred by pipette in an approximately 50 µl drop of ERS to an inverted 100 mm petri dish lid and observed in groups of about 50 embryos. To immobilize embryos for photography or detailed observation, 1 ml of a 20× stock anesthetic was added to the approximate 20 ml of ERS in a 100 mm petri dish. The 20× stock anesthetic was 3 g/L of tricaine methanesulfonate (MS-222), 20 mM Tris, pH 8, in ERS. Anesthetized embryos, with or without an intact chorion, became immobile in about 2 minutes and remained viable in this solution for at least 30 minutes. After observation, the embryos were moved to a fresh dish of ERS and regained their mobility in several minutes.

Embryos microinjected with linearized fish expression DNA vectors at the one-cell stage containing either Red II or Green II could be scored as positive for expression of fluorescent proteins within 24 hours. Typically, greater than 50% of the embryos contained fluorescent cells or patches which were retained in about 10% of the individuals upon maturity. From one of the adult fish containing a fluorescent patch of Red II expression, a line of fish has been derived in which Red II is ubiquitously expressed from the embryo through the adult.

Bibliography

Fradkov, A. F., et al. (2000) Novel Fluorescent protein from *Discosoma* coral and its mutants possesses a unique far-red fluorescence. FEBS Letters 479:127-130.

Gibbs, P. D. L.; Peek, A., and Thorgaard, G. (1994) An in vivo screen for the luciferase transgene in zebrafish. *Mol. Mar. Biol. Biotechnol.* 3:307-316.

Gibbs, P. D. L. & Schmale, M. C. (March/April 2000) GFP as a Genetic Marker Scorable Throughout the Life Cycle of Transgenic Zebrafish. Marine Biotechnology. 2:107-125.

Liu, H. S., et al. (1999) Is Green Fluorescent Protein Toxic to the Living Cells? Biochemical & Biophysical Research Communications 260:712-717.

Matz, M. V., et al. (October 1999) Fluorescent proteins from nonbioluminescent *Anthozoa* species. Nature Biotech 17:969-973.

Ormo, M., et al. (1996) Crystal structure of the *Aequorea victoria* green fluorescent protein. Science 273:1392-1395.

Yang, F., Moss, L. G., and Phillips, G. N., Jr. (1996) The Molecular Structure of GFP. Nature Biotech 14:1246-1251.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An isolated fluorescent protein that is encoded by the DNA sequence comprising SEQ ID NO:1 (Red I).

2. The fluorescent protein of claim 1, wherein the protein comprises an amino acid sequence comprising SEQ ID NO:2 (Red I).

3. The isolated fluorescent protein of claim 1, wherein the fluorescent protein comprises an amino acid substitution at position 232 of Red I of SEQ ID NO:2.

4. The isolated fluorescent protein of claim 3, wherein the fluorescent protein comprises the amino acid sequence of SEQ ID NO:8 (Green II).

5. An isolated fluorescent protein that is encoded by the DNA sequence comprising SEQ ID NO:5 (Green I).

6. The fluorescent protein of claim 5, wherein the protein comprises an amino acid sequence comprising SEQ ID NO:6 (Green I).

7. The isolated fluorescent protein of claim 5, wherein the fluorescent protein comprises an amino acid substitution at position 176 of Red I of SEQ ID NO:6.

8. The isolated fluorescent protein of claim 7, wherein the fluorescent protein comprises the amino acid sequence of SEQ ID NO:4 (Red II).

* * * * *

UNITED STATES PATENT AND TRADEMARK OFFICE
CERTIFICATE OF CORRECTION

PATENT NO. : 7,291,711 B2 Page 1 of 1
APPLICATION NO. : 11/021014
DATED : November 6, 2007
INVENTOR(S) : Gibbs et al.

It is certified that error appears in the above-identified patent and that said Letters Patent is hereby corrected as shown below:

Column 29, claim 4, line 3: Replace "SEQ ID NO:8 (Green II)", with --SEQ ID NO:4 (Red II)--.

Column 30, claim 7, line 3: Replace "Red I", with --Green I--.

Column 30, claim 8, line 3: Replace "SEQ ID NO:4 (Red II)", with --SEQ ID NO:8 (Green II)--.

Signed and Sealed this

Twenty-second Day of July, 2008

JON W. DUDAS
*Director of the United States Patent and Trademark Office*

SEQUENCE LISTING

```
<160> NUMBER OF SEQ ID NOS: 15

<210> SEQ ID NO 1
<211> LENGTH: 711
<212> TYPE: DNA
<213> ORGANISM: Artificial
<220> FEATURE:
<223> OTHER INFORMATION: mutant red fluorescent protein
<220> FEATURE:
<221> NAME/KEY: CDS
<222> LOCATION: (1)..(711)
<223> OTHER INFORMATION:

<400> SEQUENCE: 1 atg agt tgt tcc aag aat gtt atc aag gag ttc atg agg ttt aag gtt      48
Met Ser Cys Ser Lys Asn Val Ile Lys Glu Phe Met Arg Phe Lys Val
1               5                   10                  15 cgt atg gaa gga acg gtc aat ggg cac gag ttt gaa ata gaa ggc gaa      96
Arg Met Glu Gly Thr Val Asn Gly His Glu Phe Glu Ile Glu Gly Glu
            20                  25                  30 gga gaa ggg agg cca tac gaa ggc cac aat acc gta aag ctt aag gta     144
Gly Glu Gly Arg Pro Tyr Glu Gly His Asn Thr Val Lys Leu Lys Val
        35                  40                  45 acc aag ggg gga cct ttg cca ttt gct tgg gat att ttg tca cca caa     192
Thr Lys Gly Gly Pro Leu Pro Phe Ala Trp Asp Ile Leu Ser Pro Gln
```

```
                   50                  55                  60
ttt cag tat gga agc aag gta tat gtc aag cat cct gcc gac ata cca       240
Phe Gln Tyr Gly Ser Lys Val Tyr Val Lys His Pro Ala Asp Ile Pro
 65                  70                  75                  80 gac tat aaa aag ctg tca ttt cct gaa gga ttt aaa tgg gaa agg gtc       288
Asp Tyr Lys Lys Leu Ser Phe Pro Glu Gly Phe Lys Trp Glu Arg Val
                     85                  90                  95 atg aac ttt gaa gac ggt ggc gtc gtt act gta acc cag gat tcc agt       336
Met Asn Phe Glu Asp Gly Gly Val Val Thr Val Thr Gln Asp Ser Ser
                100                 105                 110 ttg cag gat ggc tgt ttc atc tac aag gtc aag ttc att ggc gtg aac       384
Leu Gln Asp Gly Cys Phe Ile Tyr Lys Val Lys Phe Ile Gly Val Asn
            115                 120                 125 ttt cct tct gat gga cct gtt atg caa aag aag aca atg ggc tgg gaa       432
Phe Pro Ser Asp Gly Pro Val Met Gln Lys Lys Thr Met Gly Trp Glu
        130                 135                 140 gcc agc act gag cgt ttg tat cct cgt gat ggc gtg ttg aaa gga gag       480
Ala Ser Thr Glu Arg Leu Tyr Pro Arg Asp Gly Val Leu Lys Gly Glu
145                 150                 155                 160 att cat aag gct ctg aag ttg aaa gac ggt ggt cat tac cta gtt gaa       528
Ile His Lys Ala Leu Lys Leu Lys Asp Gly Gly His Tyr Leu Val Glu
                165                 170                 175 ttc aaa act att tac atg gca aag aag cct gtg cag cta cca ggg tac       576
Phe Lys Thr Ile Tyr Met Ala Lys Lys Pro Val Gln Leu Pro Gly Tyr
                180                 185                 190 tac tat gtt gac tcc aaa ctg gat ata aca agc cac aac aaa gac tat       624
Tyr Tyr Val Asp Ser Lys Leu Asp Ile Thr Ser His Asn Lys Asp Tyr
            195                 200                 205 aca atc gtt gag cag tat gaa aga acc gag gga cgc cac cat ctg ttc       672
Thr Ile Val Glu Gln Tyr Glu Arg Thr Glu Gly Arg His His Leu Phe
        210                 215                 220 ctt aag gct gaa ctt ggc tca gac gtg ggt gag cgg taa                   711
Leu Lys Ala Glu Leu Gly Ser Asp Val Gly Glu Arg
225                 230                 235

<210> SEQ ID NO 2
<211> LENGTH: 236
<212> TYPE: PRT
<213> ORGANISM: Artificial
<220> FEATURE:
<223> OTHER INFORMATION: mutant red fluorescent protein

<400> SEQUENCE: 2

Met Ser Cys Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
                100                 105                 110

Leu Gln Asp Gly Cys Phe Ile Tyr Lys Val Lys Phe Ile Gly Val Asn
            115                 120                 125
```

```
Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Thr Ile Tyr Met Ala Lys Lys Pro Val Gln Leu Pro Gly Tyr
            180                 185                 190

Tyr Tyr Val Asp Ser Lys Leu Asp Ile Thr Ser His Asn Lys Asp Tyr
        195                 200                 205

Thr Ile Val Glu Gln Tyr Glu Arg Thr Glu Gly Arg His His Leu Phe
    210                 215                 220

Leu Lys Ala Glu Leu Gly Ser Asp Val Gly Glu Arg
225                 230                 235

<210> SEQ ID NO 3
<211> LENGTH: 711
<212> TYPE: DNA
<213> ORGANISM: Artificial
<220> FEATURE:
<223> OTHER INFORMATION: mutant red fluorescent protein
<220> FEATURE:
<221> NAME/KEY: CDS
<222> LOCATION: (1)..(711)
<223> OTHER INFORMATION:

<400> SEQUENCE: 3 atg agt tgt tcc aag aat gtt atc aag gag ttc atg agg ttt aag gtt      48
Met Ser Cys Ser Lys Asn Val Ile Lys Glu Phe Met Arg Phe Lys Val
1               5                   10                  15 cgt atg gaa gga acg gtc aat ggg cac gag ttt gaa ata gaa ggc gaa      96
Arg Met Glu Gly Thr Val Asn Gly His Glu Phe Glu Ile Glu Gly Glu
            20                  25                  30 gga gaa ggg agg cca tac gaa ggc cac aat acc gta aag ctt aag gta     144
Gly Glu Gly Arg Pro Tyr Glu Gly His Asn Thr Val Lys Leu Lys Val
        35                  40                  45 acc aag ggg gga cct ttg cca ttt gct tgg gat att ttg tca cca caa     192
Thr Lys Gly Gly Pro Leu Pro Phe Ala Trp Asp Ile Leu Ser Pro Gln
    50                  55                  60 ttt cag tat gga agc aag gta tat gtc aag cat cct gcc gac ata cca     240
Phe Gln Tyr Gly Ser Lys Val Tyr Val Lys His Pro Ala Asp Ile Pro
65                  70                  75                  80 gac tat aaa aag ctg tca ttt cct gaa gga ttt aaa tgg gaa agg gtc     288
Asp Tyr Lys Lys Leu Ser Phe Pro Glu Gly Phe Lys Trp Glu Arg Val
                85                  90                  95 atg aac ttt gaa gac ggt ggc gtc gtt act gta acc cag gat tcc agt     336
Met Asn Phe Glu Asp Gly Gly Val Val Thr Val Thr Gln Asp Ser Ser
            100                 105                 110 ttg cag gat ggc tgt ttc atc tac aag gtc aag ttc att ggc gtg aac     384
Leu Gln Asp Gly Cys Phe Ile Tyr Lys Val Lys Phe Ile Gly Val Asn
        115                 120                 125 ttt cct tct gat gga cct gtt atg caa aag aag aca atg ggc tgg gaa     432
Phe Pro Ser Asp Gly Pro Val Met Gln Lys Lys Thr Met Gly Trp Glu
    130                 135                 140 gcc agc act gag cgt ttg tat cct cgt gat ggc gtg ttg aaa gga gag     480
Ala Ser Thr Glu Arg Leu Tyr Pro Arg Asp Gly Val Leu Lys Gly Glu
145                 150                 155                 160 att cat aag gct ctg aag ttg aaa gac ggt ggt cat tac cta gtt gaa     528
Ile His Lys Ala Leu Lys Leu Lys Asp Gly Gly His Tyr Leu Val Glu
                165                 170                 175
```

```
ttc aaa act att tac atg gca aag aag cct gtg cag cta cca ggg tac      576
Phe Lys Thr Ile Tyr Met Ala Lys Lys Pro Val Gln Leu Pro Gly Tyr
            180                 185                 190 tac tat gtt gac tcc aaa ctg gat ata aca agc cac aac aaa gac tat      624
Tyr Tyr Val Asp Ser Lys Leu Asp Ile Thr Ser His Asn Lys Asp Tyr
            195                 200                 205 aca atc gtt gag cag tat gaa aga acc gag gga cgc cac cat ctg ttc      672
Thr Ile Val Glu Gln Tyr Glu Arg Thr Glu Gly Arg His His Leu Phe
    210                 215                 220 ctt aag gct gaa ctt ggc tca aac gtg ggt gag cgg taa                  711
Leu Lys Ala Glu Leu Gly Ser Asn Val Gly Glu Arg
225                 230                 235
```

<210> SEQ ID NO 4
<211> LENGTH: 236
<212> TYPE: PRT
<213> ORGANISM: Artificial
<220> FEATURE:
<223> OTHER INFORMATION: mutant red fluorescent protein

<400> SEQUENCE: 4

```
Met Ser Cys Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Thr Ile Tyr Met Ala Lys Lys Pro Val Gln Leu Pro Gly Tyr
            180                 185                 190

Tyr Tyr Val Asp Ser Lys Leu Asp Ile Thr Ser His Asn Lys Asp Tyr
        195                 200                 205

Thr Ile Val Glu Gln Tyr Glu Arg Thr Glu Gly Arg His His Leu Phe
    210                 215                 220

Leu Lys Ala Glu Leu Gly Ser Asn Val Gly Glu Arg
225                 230                 235
```

<210> SEQ ID NO 5
<211> LENGTH: 684
<212> TYPE: DNA
<213> ORGANISM: Artificial
<220> FEATURE:
<223> OTHER INFORMATION: mutant green fluorescent protein -continued

```
<220> FEATURE:
<221> NAME/KEY: CDS
<222> LOCATION: (1)..(684)
<223> OTHER INFORMATION:

<400> SEQUENCE: 5 atg agt gtg ata aaa cca gac atg aag atc aag ctg cgt atg gaa ggt    48
Met Ser Val Ile Lys Pro Asp Met Lys Ile Lys Leu Arg Met Glu Gly
1               5                  10                  15 gct gta aac ggg cac aag ttc gtg att gaa gga gac gga aaa ggc aag    96
Ala Val Asn Gly His Lys Phe Val Ile Glu Gly Asp Gly Lys Gly Lys
            20                  25                  30 cct ttc gag gga aaa cag act atg gac ctt aca gtc ata gaa ggc gca   144
Pro Phe Glu Gly Lys Gln Thr Met Asp Leu Thr Val Ile Glu Gly Ala
        35                  40                  45 cct ttg cct ttc gct tac gat atc ttg aca aca gta ttc gat tac ggc   192
Pro Leu Pro Phe Ala Tyr Asp Ile Leu Thr Thr Val Phe Asp Tyr Gly
    50                  55                  60 aac agg gta ttc gcc aaa tac cca aaa gac ata cca gac tat ttc aag   240
Asn Arg Val Phe Ala Lys Tyr Pro Lys Asp Ile Pro Asp Tyr Phe Lys
65                  70                  75                  80 cag acg ttt ccg gag ggg tac tcc tgg gaa cga agc atg aca tac gaa   288
Gln Thr Phe Pro Glu Gly Tyr Ser Trp Glu Arg Ser Met Thr Tyr Glu
                85                  90                  95 gac cag ggc att tgc atc gcc aca aac gac ata aca atg atg aaa ggc   336
Asp Gln Gly Ile Cys Ile Ala Thr Asn Asp Ile Thr Met Met Lys Gly
            100                 105                 110 gtc gac gac tgt ttt gtc tat aaa att cga ttt gat ggt gtg aac ttt   384
Val Asp Asp Cys Phe Val Tyr Lys Ile Arg Phe Asp Gly Val Asn Phe
        115                 120                 125 cct gcc aat ggt cca gtt atg cag agg aag acg cta aaa tgg gag cca   432
Pro Ala Asn Gly Pro Val Met Gln Arg Lys Thr Leu Lys Trp Glu Pro
    130                 135                 140 tcc act gaa aaa atg tat gtg cgt gat ggg gta ctg aag ggt gat gtt   480
Ser Thr Glu Lys Met Tyr Val Arg Asp Gly Val Leu Lys Gly Asp Val
145                 150                 155                 160 aac atg gct ctg ttg ctt gaa gga ggt ggc cat tac cga tgt gac tcc   528
Asn Met Ala Leu Leu Leu Glu Gly Gly Gly His Tyr Arg Cys Asp Ser
                165                 170                 175 aaa act act tac aaa gct aag aag gtt gtc cag ttg cca gac tat cat   576
Lys Thr Thr Tyr Lys Ala Lys Lys Val Val Gln Leu Pro Asp Tyr His
            180                 185                 190 ttt gtt gac cat cgc att gag att gtg agc cac gac aaa gat tac aac   624
Phe Val Asp His Arg Ile Glu Ile Val Ser His Asp Lys Asp Tyr Asn
        195                 200                 205 aag gtt aag ctg tat gag cat gcc gaa gct cat tct ggg ctg ccg agg   672
Lys Val Lys Leu Tyr Glu His Ala Glu Ala His Ser Gly Leu Pro Arg
    210                 215                 220 cag gcc aag taa                                                    684
Gln Ala Lys
225

<210> SEQ ID NO 6
<211> LENGTH: 227
<212> TYPE: PRT
<213> ORGANISM: Artificial
<220> FEATURE:
<223> OTHER INFORMATION: mutant green fluorescent protein

<400> SEQUENCE: 6

Met Ser Val Ile Lys Pro Asp Met Lys Ile Lys Leu Arg Met Glu Gly
1               5                  10                  15
```

```
Ala Val Asn Gly His Lys Phe Val Ile Glu Gly Asp Gly Lys Gly Lys
            20                  25                  30

Pro Phe Glu Gly Lys Gln Thr Met Asp Leu Thr Val Ile Glu Gly Ala
            35                  40                  45

Pro Leu Pro Phe Ala Tyr Asp Ile Leu Thr Thr Val Phe Asp Tyr Gly
            50                  55                  60

Asn Arg Val Phe Ala Lys Tyr Pro Lys Asp Ile Pro Asp Tyr Phe Lys
65                      70                  75                  80

Gln Thr Phe Pro Glu Gly Tyr Ser Trp Glu Arg Ser Met Thr Tyr Glu
                    85                  90                  95

Asp Gln Gly Ile Cys Ile Ala Thr Asn Asp Ile Thr Met Met Lys Gly
                    100                 105                 110

Val Asp Asp Cys Phe Val Tyr Lys Ile Arg Phe Asp Gly Val Asn Phe
                115                 120                 125

Pro Ala Asn Gly Pro Val Met Gln Arg Lys Thr Leu Lys Trp Glu Pro
            130                 135                 140

Ser Thr Glu Lys Met Tyr Val Arg Asp Gly Val Leu Lys Gly Asp Val
145                 150                 155                 160

Asn Met Ala Leu Leu Leu Glu Gly Gly Gly His Tyr Arg Cys Asp Ser
                165                 170                 175

Lys Thr Thr Tyr Lys Ala Lys Lys Val Val Gln Leu Pro Asp Tyr His
                180                 185                 190

Phe Val Asp His Arg Ile Glu Ile Val Ser His Asp Lys Asp Tyr Asn
            195                 200                 205

Lys Val Lys Leu Tyr Glu His Ala Glu Ala His Ser Gly Leu Pro Arg
            210                 215                 220

Gln Ala Lys
225

<210> SEQ ID NO 7
<211> LENGTH: 684
<212> TYPE: DNA
<213> ORGANISM: Artificial
<220> FEATURE:
<223> OTHER INFORMATION: mutant green fluorescent protein
<220> FEATURE:
<221> NAME/KEY: CDS
<222> LOCATION: (1)..(684)
<223> OTHER INFORMATION:

<400> SEQUENCE: 7 atg agt gtg ata aaa cca gac atg aag atc aag ctg cgt atg gaa ggt     48
Met Ser Val Ile Lys Pro Asp Met Lys Ile Lys Leu Arg Met Glu Gly
1               5                   10                  15 gct gta aac ggg cac aag ttc gtg att gaa gga gac gga aaa ggc aag     96
Ala Val Asn Gly His Lys Phe Val Ile Glu Gly Asp Gly Lys Gly Lys
            20                  25                  30 cct ttc gag gga aaa cag act atg gac ctt aca gtc ata gaa ggc gca    144
Pro Phe Glu Gly Lys Gln Thr Met Asp Leu Thr Val Ile Glu Gly Ala
            35                  40                  45 cct ttg cct ttc gct tac gat atc ttg aca aca gta ttc gat tac ggc    192
Pro Leu Pro Phe Ala Tyr Asp Ile Leu Thr Thr Val Phe Asp Tyr Gly
            50                  55                  60 aac agg gta ttc gcc aaa tac cca aaa gac ata cca gac tat ttc aag    240
Asn Arg Val Phe Ala Lys Tyr Pro Lys Asp Ile Pro Asp Tyr Phe Lys
65                  70                  75                  80 cag acg ttt ccg gag ggg tac tcc tgg gaa cga agc atg aca tac gaa    288
Gln Thr Phe Pro Glu Gly Tyr Ser Trp Glu Arg Ser Met Thr Tyr Glu
```

|  |  |
|---|---|
| gac cag ggc att tgc atc gcc aca aac gac ata aca atg atg aaa ggc<br>Asp Gln Gly Ile Cys Ile Ala Thr Asn Asp Ile Thr Met Met Lys Gly<br>                    100                    105                    110 | 336 |
| gtc gac gac tgt ttt gtc tat aaa att cga ttt gat ggt gtg aac ttt<br>Val Asp Asp Cys Phe Val Tyr Lys Ile Arg Phe Asp Gly Val Asn Phe<br>            115                    120                    125 | 384 |
| cct gcc aat ggt cca gtt atg cag agg aag acg cta aaa tgg gag cca<br>Pro Ala Asn Gly Pro Val Met Gln Arg Lys Thr Leu Lys Trp Glu Pro<br>130                    135                    140 | 432 |
| tcc act gaa aaa atg tat gtg cgt gat ggg gta ctg aag ggt gat gtt<br>Ser Thr Glu Lys Met Tyr Val Arg Asp Gly Val Leu Lys Gly Asp Val<br>145                    150                    155                    160 | 480 |
| aac atg gct ctg ttg ctt gaa gga ggt ggc cat tac cga tgt gac ttc<br>Asn Met Ala Leu Leu Leu Glu Gly Gly Gly His Tyr Arg Cys Asp Phe<br>            165                    170                    175 | 528 |
| aaa act act tac aaa gct aag aag gtt gtc cag ttg cca gac tat cat<br>Lys Thr Thr Tyr Lys Ala Lys Lys Val Val Gln Leu Pro Asp Tyr His<br>            180                    185                    190 | 576 |
| ttt gtt gac cat cgc att gag att gtg agc cac gac aaa gat tac aac<br>Phe Val Asp His Arg Ile Glu Ile Val Ser His Asp Lys Asp Tyr Asn<br>                195                    200                    205 | 624 |
| aag gtt aag ctg tat gag cat gcc gaa gct cat tct ggg ctg ccg agg<br>Lys Val Lys Leu Tyr Glu His Ala Glu Ala His Ser Gly Leu Pro Arg<br>210                    215                    220 | 672 |
| cag gcc aag taa<br>Gln Ala Lys<br>225 | 684 |

<210> SEQ ID NO 8
<211> LENGTH: 227
<212> TYPE: PRT
<213> ORGANISM: Artificial
<220> FEATURE:
<223> OTHER INFORMATION: mutant green fluorescent protein

<400> SEQUENCE: 8

Met Ser Val Ile Lys Pro Asp Met Lys Ile Lys Leu Arg Met Glu Gly
1               5                   10                  15

Ala Val Asn Gly His Lys Phe Val Ile Glu Gly Asp Gly Lys Gly Lys
            20                  25                  30

Pro Phe Glu Gly Lys Gln Thr Met Asp Leu Thr Val Ile Glu Gly Ala
        35                  40                  45

Pro Leu Pro Phe Ala Tyr Asp Ile Leu Thr Thr Val Phe Asp Tyr Gly
    50                  55                  60

Asn Arg Val Phe Ala Lys Tyr Pro Lys Asp Ile Pro Asp Tyr Phe Lys
65                  70                  75                  80

Gln Thr Phe Pro Glu Gly Tyr Ser Trp Glu Arg Ser Met Thr Tyr Glu
                85                  90                  95

Asp Gln Gly Ile Cys Ile Ala Thr Asn Asp Ile Thr Met Met Lys Gly
            100                 105                 110

Val Asp Asp Cys Phe Val Tyr Lys Ile Arg Phe Asp Gly Val Asn Phe
        115                 120                 125

Pro Ala Asn Gly Pro Val Met Gln Arg Lys Thr Leu Lys Trp Glu Pro
    130                 135                 140

Ser Thr Glu Lys Met Tyr Val Arg Asp Gly Val Leu Lys Gly Asp Val
145                 150                 155                 160

Asn Met Ala Leu Leu Leu Glu Gly Gly Gly His Tyr Arg Cys Asp Phe

-continued

```
                165                 170                 175
Lys Thr Thr Tyr Lys Ala Lys Val Val Gln Leu Pro Asp Tyr His
            180                 185                 190

Phe Val Asp His Arg Ile Glu Ile Val Ser His Asp Lys Asp Tyr Asn
            195                 200                 205

Lys Val Lys Leu Tyr Glu His Ala Glu Ala His Ser Gly Leu Pro Arg
            210                 215                 220

Gln Ala Lys
225

<210> SEQ ID NO 9
<211> LENGTH: 45
<212> TYPE: RNA
<213> ORGANISM: Artificial
<220> FEATURE:
<223> OTHER INFORMATION: adaptor

<400> SEQUENCE: 9
gcugauggcg augaaugaac acugcguuug cuggcuuuga ugaaa          45

<210> SEQ ID NO 10
<211> LENGTH: 41
<212> TYPE: DNA
<213> ORGANISM: Artificial
<220> FEATURE:
<223> OTHER INFORMATION: primer

<400> SEQUENCE: 10
ctcgagaagc ttgaattcgg atccttttttt tttttttttt t             41

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
gctgatggcg atgaatgaac actg                                 24

<210> SEQ ID NO 12
<211> LENGTH: 33
<212> TYPE: DNA
<213> ORGANISM: Artificial
<220> FEATURE:
<223> OTHER INFORMATION: primer

<400> SEQUENCE: 12
ccggtaccta aggaggccac catgagttgt tcc                       33

<210> SEQ ID NO 13
<211> LENGTH: 37
<212> TYPE: DNA
<213> ORGANISM: Artificial
<220> FEATURE:
<223> OTHER INFORMATION: primer

<400> SEQUENCE: 13
ccggtaccta aggaggccac catgagtgtg ataaaac                   37

<210> SEQ ID NO 14
<211> LENGTH: 25
<212> TYPE: DNA
<213> ORGANISM: Artificial
```

-continued

```
<220> FEATURE:
<223> OTHER INFORMATION: primer

<400> SEQUENCE: 14
ccactagtct agatcattac cgctc                                    25

<210> SEQ ID NO 15
<211> LENGTH: 24
<212> TYPE: DNA
<213> ORGANISM: Artificial
<220> FEATURE:
<223> OTHER INFORMATION: primer

<400> SEQUENCE: 15
ggtctagatt acttggcctg cctc                                     24
```